US006858389B1

(12) United States Patent
Kopchick et al.

(10) Patent No.: US 6,858,389 B1
(45) Date of Patent: Feb. 22, 2005

(54) GROWTH HORMONE-REGULATABLE LIVER GENES AND PROTEINS, AND USES THEREOF

(75) Inventors: John Joseph Kopchick, Athens, OH (US); Jean Tiong, Berwood, MD (US)

(73) Assignee: Ohio University, Athens, OH (US)

(*) Notice: Subject to any disclaimer, the term of this patent is extended or adjusted under 35 U.S.C. 154(b) by 0 days.

(21) Appl. No.: 09/959,716

(22) PCT Filed: May 5, 2000

(86) PCT No.: PCT/US00/12366

§ 371 (c)(1),
(2), (4) Date: Mar. 11, 2002

(87) PCT Pub. No.: WO00/66787

PCT Pub. Date: Nov. 9, 2000

Related U.S. Application Data
(60) Provisional application No. 60/132,663, filed on May 5, 1999.

(51) Int. Cl.$^7$ ............................ C12Q 1/68; G01N 33/53
(52) U.S. Cl. ............................................. 435/6; 435/7.1
(58) Field of Search ..................................... 435/7.1, 6

(56) References Cited

U.S. PATENT DOCUMENTS 5,350,836 A    9/1994  Kopchick et al. ........... 530/399

FOREIGN PATENT DOCUMENTS

EP              0158973         4/1985

OTHER PUBLICATIONS

Adan et al., *Diagnostic Markers of Permanent Idiopathic Growth Hormone Deficiency*, Journal of Clinical Endocrinology and Metabolism, vol. 78, No. 2, pp. 353–358, 1994.
Alexander et al., *The effect of social stress on adrenal axis activity in horses: the importance of monitoring corticosteroid–binding globulin capacity*, Journal of Endocrinology, No. 157, pp. 425–432.
Banine et al., *Positive and negative elements modulate the promotor of the human liver–specific 2–HS–glycoprotein gene*, Eur. J. Biochem, No. 267, pp. 1214–1222, Feb. 2000.
Braun et al., *A novel human muscle factor related to but distinct from MyoD1 induces myogenic conversion in 10T1/2 fibroblasts*, The EMBO Journal, vol. 8, No. 3, pp. 701–709, 1989.
Chan et al., *Molecular Cloning and Localization to Chromosome 6 of Mouse INT1L1 Gene*, Somatic Cell and Molecular genetics, vol. 15, No. 6, pp. 555–562, 1989.
Costa et al., *Transgenic rabbits overexpressing growth hormone develop acromegaly and diabetes mellitus*, The FASEB Journal, vol. 12, pp. 1455–1460, Nov. 1998.
Dantoine et al, *Decrease of Serum Paraoxonase Activity in Chronic Renal Failure*, Journal of the American Society of Nephrology 9, pp. 2082–2088, Nov. 1998.

Galizzi et al, *Molecular cloning of a cDNA encoding the human interleukin 4 receptor.* International Immunology, vol. 2, No. 7, pp. 669–675, 1990.
Gregoraszczuk et al., *Response of porcine theca and granulosa cells to GH during short–term in vitro culture*, Animal Reproduction Science 58, pp. 113–125, Feb. 2000.
He et al., *Molecular Cloning Of Androgen Receptors From Divergent Species With A Polymerase Chain Reaction Technique: Complete cDNA Sequence Of The Mouse Androgen Receptor And Isolation Of Androgen Receptor cDNA Probes From Dog, Guinea Pig And Clawed Frog*, Biochemical and Biophysical Research Communications, vol. 171, No. 2, pp. 697–704, Sep. 1990.
Robert A. Hegele, *Paraoxonase genes and disease*, The Finnish Medical Society Duodecim, Ann Med., No. 31, pp. 217–224, Jun. 1999.
Hermansson et al., *Measurement of Human Growth Hormone Receptor Messenger Ribonucleic Acid by a Quantitative Polymerase Chain Reaction–Based Assay: Demonstration of Reduced Expression after Elective Surgery*, Journal of Clinical Endocrinology and Metabolism, vol. 82, No. 2, pp. 421–428, 1997.
Iwata et al., *Structure of the Mouse Tyrosine Hydroxylase Gene*, Biochemical and Biophysical Research Communications, vol. 182, No. 1, pp. 348–354, Jan. 1992.
Jansson et al., *Plasma growth hormone pattern and androgens influence the levels of corticosteroid–binding globulin in rat serum*, Journal of Endocrinology, No. 122, pp. 725–732, Sep. 1989.
Kalaby et al., *Human Recombinant Alpha2–HS Glycoprotein is Produced in Insect Cells as a Full Length Inhibitor of the Insulin Receptor Tyrosine Kinase*, Horm. Metab. Res. 30, pp. 1–6, Jan. 1998.
Kohler et al., *Molecular Cloning of Mouse Glycolate Oxidase*, The Journal of Biological Chemistry, vol. 274, No. 4, pp. 2401–2407, Jan. 1999.
Kopchick et al., *Transgenic Models of Growth Hormone Action*, Annual Rev. Nutr., vol. 19, pp. 437–461, 1999.
Lemmey et al., *Differential regulation of tissue insulin–like growth factor–binding protein (IGFBP)–3, IGF–I and IGF type 1 receptor mRNA levels, and serum IGF–1 and IGFBP concentrations by growth hormone and IGF–I*, Journal of Endocrinology, vol. 154, No. 2, pp. 319–328, 1997.
Malhotra et al., *Identification of differentially expressed mRNAs in human fetal liver across gestation*, Nucleic Acids Research, vol. 27, No. 3, pp. 839–847, Feb. 1999.
Marschall et al., *Human Liver Class I Alcohol Dehydrogenase Isozyme: The Sole Cytosolic 3 –Hydroxysteroid Dehydrogenase of Iso Bile Acids*, Hepatology, vol. 31, No. 4, pp. 990–996, Apr. 2000.

(List continued on next page.)

Primary Examiner—Kenneth R. Horlick
(74) Attorney, Agent, or Firm—Iver P. Cooper

(57) ABSTRACT

Growth homone-regulatable liver genes and proteins are described. These may be used as diagnostic markers of liver pathology.

21 Claims, No Drawings

OTHER PUBLICATIONS

Mizukoshi et al., *Serum Levels of Soluble Interferon Alfa/Beta Receptor as an Inhibitory Factor of Interferon in the Patients With Chronic Hepatitis C,* Hepatology, vol. 30, No. 5, pp. 1325–1331, Nov. 1999.

Nahmias et al., *Molecular characterization of the mouse 3–adrenergic receptor: relationship with the atypical receptor of adipocytes,* The EMBO Journal, vol. 10, No. 12, pp. 3721–3727, 1991.

Panduro et al., *Liver–Specific Gene Expression in Various Pathophysiologic States,* Hepatology, vol. 7, No. 1, pp. 10S–18S, 1987.

Quaife et al., *Histopathology Associated with Elevated Levels of Growth Hormone and Insulin–Like Growth Factor I in Transgenic Mice,* Endocrinology, vol. 124, No. 1, 1989.

Ren et al., *In its active form, the GTP–binding protein rab8 interacts with a stress–activated protein kinase,* Proc. Natl. Acad. Sci. USA, vol. 93, pp. 5151–5155, May 1996.

Saggese et al., *Diagnosis and Treatment of Growth Hormone Deficiency in Children and Adolesents: Towards a Consensus,* Hormone Research, vol. 50, pp. 320–340, Dec. 1998.

Sharp et al., *Expression of an Ovine Growth Hormone Transgene in Mice Causes Organomegaly and Hepatic Lesions Which Resolve Following Transgene Inactivation,* Laboratory Animal Science, vol. 45, No. 5, Oct. 1995.

Shen et al., *Cirrhotic Liver Expresses Low Levels of the Full–Length and Truncated Growth Hormone Receptors,* Journal of Clinical Endocrinology and Metabolism, vol. 83, No. 7, Jul. 1998.

Soto et al., *Rib Metastasis Revealing Hepatocellular Carcinoma,* Scand. J. Gastroenterol, vol. 35, pp. 333–336, 2000.

Le Stunff et al., *Growth Hormone Stimulates Interferon Regulatory Factor–1 Gene Expression in the Liver,* Endocrinology, vol. 139, No. 3, pp. 859–866, Mar. 1998.

Sumimoto et al., *Complementary DNA for the Mouse Homolog of the Small Subunit of Human Cytochrome $_{558}$,* Biochemical and Biophysical Research Communications, vol. 165, No. 2, pp. 902–906, Dec. 1989.

Van Kerkhof et al., *Endocytosis and Degradation of the Growth Hormone Receptor Are Proteasome–dependent,* The Journal of Biological Chemistry, vol. 275, No. 3, pp. 1575–1580, Jan. 2000.

Wang et al., *3–Hydroxy–3–methylglutaryl coenzyme A lyase (HL): cloning and characterization of a mouse liver HL cDNA and subchromosomal mapping of the human and mouse HL genes,* Mammalian Genome, vol. 4, pp. 382–387, 1993.

Yang et al., *Glomerulosclerosis and Body Growth Are Mediated by Different Portions of Bovine Growth Hormone,* Laboratory Investigation, vol. 68, No. 1, pp. 62–70, 1993.

Yatsuhashi et al., *Immunohistochemical analysis of hepatic interferon alpha–beta receptor level: relationship between receptor expression and response to interferon therapy in patients with chronic hepatitis C,* Journal of Hepatology, vol. 30, No. 6, pp. 995–1003, Jun. 1999.

GROWTH HORMONE-REGULATABLE LIVER GENES AND PROTEINS, AND USES THEREOF

REFERENCE TO RELATED APPLICATIONS

The present application is the national stage under 35 U.S.C. 371 of international application PCT/US00/12366, filed May 5, 2000 which designated the United States, and which international application was published under PCT Article 21(2) in the English language.

PCT/US00/12366 is a nonprovisional of Provisional Ser. No. 60/132,663, filed May 5, 1999.

BACKGROUND OF THE INVENTION

1. Field of the Invention

This invention relates to the diagnosis of abnormal GH activity or general pathological activity in the liver.

2. Description of the Background Art

Growth Hormones

The growth hormones are vertebrate proteins with about 191 amino acid residues, the number varying from species to species. There are four cysteine residues, and two disulfide bridges. The 3D-structure of porcine GH is known; it is composed of four major antiparallel alpha-helices, at residues 7–34, 75–87, 106–127 and 152–183.

The 3D structure of the hGH:hGH receptor complex is also known. Each molecule of hGH binds two molecules of the receptor. hGH binds to two binding sites on hGH receptor. Helix 4, the loop residues 54–74, and, to a lesser extent, helix 1, mediate binding to binding site 1. Helix 3 mediates binding to binding site 2.

See generally Harvey, et al., *Growth Hormone* (CRC Press: 1995).

GH is synthesized and secreted by the somatotrophic and somatomammotrophic cells of the lateral anterior pituitary. The control of GH production and secretion is complex, but is mainly under the influence of growth hormone releasing hormone (GHRH) and somatostatin, which stimulate and inhibit it, respectively. The shifting balance between these regulatory agents is responsible for the pulsatile nature of GH secretion, with normal human concentrations ranging from a baseline value <1 μg/L to peaks of 25–50 μg/L. Glucocorticoids and thyroid hormones, and various carbohydrates, amino acids, fatty acids and other biomolecules, are also known to directly or indirectly regulate GH secretion.

Most GH is secreted at night, during deep sleep, but some is secreted in response to exercise and other forms of physical stress. About 500 μg/m2 body surface area are secreted by women, and 350 by men. GH secretion rates are highest in adolescents and lowest in the elderly. GH has a plasma half life of about 20–25 min. and is cleared at a rate of 100–150 ml/m2 body surface area.

Metabolic and Clinical Effects of Growth Hormone

Chronic elevation of growth hormone levels in humans usually results in either gigantism or acromegaly. GH, besides affecting skeletal growth, can also influence other organ systems, in particular, the liver and kidney. In the kidney, it has been associated with glomerulosclerosis and nephropathy. (Diabetic glumerosclerosis and nephropathy has been attributed to a GH effect.) In the liver, it has been shown to cause an increase in liver size, as a consequence of both hyperplasia and hepatocyte hypertrophy. The hepatocellular lesions associated with high GH levels progress with age. See Quaife, et al, Endocrinol., 124: 49 (1989); Sharp, et al., Lab. Anim. Sci., 45:607–612 (1995).

There is reason to believe that excessive GH activity in the liver is deleterious to health. Mice that express GH transgenes typically live to only about one year of age, while the normal life expectancy for mice is 2–2.5 years. A major cause of death in the GH transgenic mice has been liver disease.

Chronic depression of GH levels can also impair health.

Growth Hormone Antagonists

In view of the foregoing, it has been suggested that if a subject is suffering from excessive GH activity, it can be useful to inhibit such activity by inhibiting the production, release or action of GH, or facilitating the elimination of GH.

Among the agents useful for this purpose are those which are competitive binding antagonists of GH. It was discovered that certain mutants of the third alpha helix of GH are useful for this purpose. Kopchick, U.S. Pat. No. 5,350,836.

In order to determine whether it is appropriate to initiate or terminate use GH antagonists or other GH-inhibiting drugs, it is important to be able to monitor GH activity.

Monitoring of GH Activity

The most straightforward marker of GH activity is the serum level of GH per se. For humans, the mean GH concentration (ug/L) in blood is

| | | |
|---|---|---|
| preadolescent | 4.6 | |
| early adolescent | 4.8 | |
| late adolescent | 13.8 | |
| adult | 1.8 | |
| ISS (10y old) | 3.5 | |
| GH deficient | 1.4 | |
| IDDM (boys) | 9.0 | |
| Obese (male) | 0.66 | (lower than controls) |
| Fasting | 6.7 | (higher than controls) |
| Hyperthyroid | 1.9 | (higher than controls) |

ISS = idiopathic short stature, IDDM = insulin dependent diabetes mellitus
See Harvey (1995), supra While there is definitely a correlation between high levels of GH in serum, and high levels of GH activity, it must be recognized that both the total number of GH receptors, and the distribution of those receptors among the various organs, will vary from individual to individual. Hence, in determining whether an individual is suffering from excessive GH activity, and prone to develop adverse clinical sequelae, it is helpful to identify a metabolite which is produced or released in direct or indirect response to GH and, in particular, one which is substantially liver-specific so that the specific threat to liver function can be assessed.

Another marker of GE activity is insulin-like growth factor-1 (IGF-1). IGF-1 is a 70 amino acid single chain protein, with some structural similarity to proinsulin, which is closely regulated by GH secretion. While the majority of IGF-1 synthesis occurs in the liver, many other tissues, including bone and skeletal muscle, also release IGF-1 in response to GH. IGF-1 levels have been used by clinicians to confirm suspected cases of acromegaly.

However, it would be desirable to have a marker, or combination of markers, which was more liver specific than IGF-1, for use in monitoring and predicting the effect of chronic elevation of GH levels on liver function. It is known that mice transgenic for IGF-1 do not develop the same abnormalities as mice transgenic for GH, in particular, they do not develop similar liver and kidney abnormalities. See Quafe, supra, and Yang, et al., Lab. Invest., 68:62–70 (1993).

SUMMARY OF THE INVENTION

Applicants have identified certain genes whose expression in liver cells is elevated as a result of higher than normal GH levels. In contrast, Applicants were unable to identify similarly GH-regulated genes in kidney cells.

By use of nucleic acid binding agents to bind messenger RNA transcripts produced by the transcription of any of these genes (or to bind the corresponding complementary DNAs synthesized in vitro), or by use of a protein binding agent to bind a protein encoded by any of these genes, it is possible to assay the level of transcription of the gene in question, or the level of expression and secretion of the corresponding protein, and to correlate such level with the level of GH activity in the liver.

In addition, transgenic mammals, especially mice, rats and rabbits, which overproduce these proteins may be useful as animal models of liver pathologies.

Finally, agents which inhibit expression of these proteins (i.e., antisense nucleic acids) or the binding of these proteins to their receptors (by binding either the protein or the receptor) may be useful therapeutically in inhibiting the development of liver pathologies associated with the expression of that protein.

DETAILED DESCRIPTION OF THE PREFERRED EMBODIMENTS OF THE INVENTION

We have determined some of the differences in the patterns of gene expression between transgenic mice with a giant phenotype and nontransgenic mice with a normal phenotype. This is indicative of the effect of overproduction of GH on the expression of other genes. GH-mediated liver pathology is presumably the result of such expression.

Results of BLAST sequence similarity analyses identified several genes in the GH TG subtraction library suggesting that they are differentially expressed in GH TG mouse liver. These include interferon-$\alpha/\beta$ receptor (IFNR$\alpha\beta$), corticosteroid binding globulin (CBG), $\alpha$-fetoprotein, cytochrome P450, fetuin (Ahsg), 3-$\beta$-hydroxysteroid (3$\beta$HSD), paraoxonase-3 (PON-3), rab8 interacting protein and coagulation factor V. We have also identified two previously unknown genes affected by GH, cDNAs 5 and 45. This differential expression has been confirmed, in the case of IFNR$\alpha\beta$ and CBG, by using the differentially expressed cDNAs as probes. 3-$\beta$-hydrosteroid dehydrogenase is down-regulated, the others are up-regulated.

Assays for expression of these genes may be useful in the diagnosis of liver pathologies. Such diagnosis is not limited to the diagnosis of liver pathologies associated with giantism or acromegaly, or with diabetes, as other causative agents may act directly or indirectly upon the same genes.

Liver pathologies include:
1. Liver cirrhosis (hepatic disease of various etiology) such as
    Alcoholic liver disease
    portal hypertension
2. Liver tumor:
    Benign: adenomas and focal nodular hyperplasia
    Malignant: primary carcinomas and metastatic tumors
3. Infections of the liver: viral hepatitis and liver abscesses of whatever origin
4. Hepatic failure or deterioration of the liver function due to some chronic progressive disorder or acute injuries or massive necrosis
5. Drug related liver injury due to hepatotoxicity of therapeutic agents Reference to the pathologies is: Cotran, R. S., Kumar, V., Robbins, S. L. 1989. *Robbin's Pathologic Basis of Disease* (4th ed.) W.B. Saunders Co.; Philadelphia, Pa.; pp. 911–980.

By preliminary screening assays using nucleic acids, antibodies, or other binding agents, carried out an mRNA, cDNA or protein samples from cells of various livers with known pathologic lesions, we may determine whether the level of expression of each of the genes mentioned above is correlated with the presence (or degree of severity) of a particular liver lesion.

Also, we may make transgenic mammals (e.g. mice) that overexpress the cDNA in a liver-specific manner (using a liver-specific promoter like the albumin or PEPCK promoter), and determine if these transgenic mammals develop liver histopathologies, or other signs of aging (GH transgenic mice die prematurely of liver and kidney disease).

Conversely, transgenic mammals in which expression of these genes is knocked out can be examined to determine if they provide any protection to the liver against any of the agents known to cause liver pathology, e.g., viral infection (esp. hepatitis), alcoholism, hepatoxic drugs, tumors, etc. if so, then an agent interfering with the expression or activity of the gene product would have therapeutic value.

The proteins of interest include both secreted and intracellular proteins.

Secreted proteins can potentially disrupt normal signaling mechanisms through ligand/receptor interaction. They can also be used as indicators of a pathophysiological state. Also, they may be "peptide hormones". Thus, they could have diagnostic or therapeutic value. Depending upon the scenario, recombinant agonists or antagonists may emerge from these molecules.

Intracellular proteins, on the other hand, could regulate the intrinsic biological functions of certain cells. These proteins could be potential drug targets in that one may design molecules to activate or inhibit them.

1. $\alpha$-fetoprotein—Closely related to serum albumin but is found primarily during fetal development, during which elevated levels can be indicative of neural tube defects. Elevated levels have been reported in patients with alcoholic liver disease and hepatocellular calcinoma (HCC). [*Scand J Gastroenterol* 2000 March;35(3):333–6] This is a secreted protein.
2. Fetuin (AHSG)—A 52 kDa glycoprotein that has been reported to be an inhibitor of the insulin receptor tyrosine kinase. [Kalabay L, *Horm Metab Res* 1998 January;30(1):1–6] AHSG has also been reported to inhibit protease activities and to act as a regulator of calcium metabolism and osteogenesis. [Banine F, et al. *Eur J Biochem* 2000 February;267(4):1214–22] This protein may be important in GH's diabetogenic activity. Elimination or down regulation of this activity may allow cells to become more sensitive to the action of insulin. Thus, inhibitors of this action could be used as "insulin sensitizers".
3. 3-$\beta$-Hydroxysteroid Dehydrogenase (3-$\beta$-HSD)— Isomerase and Dehydrogenase that plays an important role in all aspects of steroid production. It is present in many different isoforms which indicates multiple functionality. It acts in the liver as a key enzyme in the cholesterol biosynthetic pathway and as a transporter of bile acids [Marscall H U, et al. *Hepatology* 2000 April;31 (4):990–6] It has also been reported that GH administration to cultured cells stimulated the activity of 3-$\beta$-HSD. [Gregoraszczuk E L, et al. *Anim Reprod Sci* 2000 February 28;58(1–2):113–25] Since the activity goes up in the livers of these GH animals and since it has been shown to be involved in cholesterol synthesis, it could be used as a target for the down regulation of cholesterol production.
4. Rab8 interacting protein—Rab proteins are small GTP binding proteins involved in vesicular transport during endocytosis and exocytosis. They are distant relatives of the ras family of oncogenes, but are not oncogenic themselves. Rab8ip shows similarity to the GC kinase, a serine/threonine kinase that has recently been identified in stress activated human lymphoid tissue. It is thought that Rab8ip may have a role in modulation of secretion in response to stress stimuli. [Ren M, et al. *Proc Natl Acad Sci USA* 1996 May 14;93(10):5151–5]

5. Paraoxonase 3 (PON3)—Although little is known about PON3, the PON family of gene products are active in cholesterol biosynthesis. PON1 is an enzyme found in serum which is associated with high density lipoprotein (HDL) and is thought to protect low density lipoprotein (LDL) from peroxidation. Decreased activity of PON enzymes is found in sufferers of chronic renal failure. [Dantoine T F, *J Am Soc Nephrol* 1998 November;9(11) :2082–8] There has been recent speculation as to the merit of potential testing for genetic variation in the PON gene family or whether the gene products might be good candidates for therapeutic interventions. [Hegele R A, *Ann Med* 1999 June;31(3):217–24]

6. S-2-hydroxy acid oxidase (Glycolate oxidase)—This gene was just recently cloned in mice. [Kohler S A, *J Biol Chem* 1999 Jan. 22;274(4):2401–7] It is a peroxisomal protein that is involved in the oxidation of hydroxy acids such as L-lactate. Any method to reduce lactic acid in a diabetic individual would be beneficial.

7. Interferon α/β receptor (IFNαβR)—Interferons are antiviral, antiproliferative, immune responsive cytokines. Recombinant forms have been in use for the treatment of various malignancies. Serum levels of soluble IFNαβR have been found to be elevated in patients with chronic hepatitis C. [Mizukoshi E, et al. *Hepatology* 1999 November;30(5):1325–31] It is thought that resistance to IFN therapy in patients with chronic hepatitis C may be due to low levels of hepatic IFNαβR. [Yatsuhashi H, *J Hepatol* 1999 June;30(6):995–1003]. Thus any method by which this IFN "binding protein" would be increased could be beneficial. Since the soluble version of this has been found, and it is secreted, it could be used as a diagnostic marker.

8. Growth Hormone Receptor (GHR)—All physiological attributes of growth hormone are mediated via signaling though binding with the GHR. Low levels of GHR have been indicated in cirrhotic liver. [Shen X Y, *J Clin Endocrinol Metab* 1998 July;83(7):2532–8]

9. Cytochrome P450—The cytochromes are an extensive family of Heme containing electron transport molecules found in liver microsomes. They convert a wide range of substrates to forms that are more easily excreted by the cell, some of which may be carcinogenic. The cytochromes are also involved in steroid and prostaglandin biosynthesis.

10. Proteosome subunit Z—A component of the multicatalytic Proteinase complex found in the eukaryotic cytosol and nucleus that is responsible for ubiquitin dependent protein degradation. It has recently been reported that GHR internalization requires proteosome action and active ubiquitin conjugation system. [van Kerkhof P, *J Biol Chem* 2000 Jan. 21;275(3):1575–80] Any substance that could control ubiquitination could be of value.

11. Corticosteroid Binding Globulin (CBG)—The major function of CBG is to regulate the bioavailability of plasma cortisol by restriction it's exit from the capillaries. [Alexander S L, *J Endocrinol* 1998 June;157(3):425–32] CBG is regulated by many factors, including stress, steroid sex hormones, and GH (when dosed continuously). [Jansson J O, *J Endocrinol* 1989 September;122(3):725–32]

12. Coagulation Factor V—Coagulation factors are a group of protease enzymes and cofactors involved in clotting. Their activation is triggered by tissue injury and phospholipoprotein release, which ultimately leads to the production of thrombin. Again, any substance that could up or down regulated blood clotting could be of value.

Definitions

Two proteins are cognate if they are produced in different species, but are sufficiently similar in structure and biological activity to be considered the equivalent proteins for those species. If the accepted scientific names for two proteins are the same but for the species identification (e.g., human GH and shark GH), they should be considered cognate. If not, the two proteins may still be considered cognate if they have at least 50% amino acid sequence identity (when globally aligned with a pam250 scoring matrix with a gap penalty of the form $q+r(k-1)$ where k is the length of the gap, $q=-12$ and $r=-4$; percent identity=number of identities as percentage of length of shorter sequence) and at least one biological activity in common.

Two genes are cognate if they are expressed in different species and encode cognate proteins.

Gene expression may be said to be specific to a particular tissue if the average ratio of the specific mRNA to total mRNA for the cells of that tissue is at least 10% higher than the average ratio is for the cells of some second tissue. Absolute specificity is not required. Hence, a gene may be said to be expressed specifically in more than one tissue.

When the term "specific" is used in this specification, absolute specificity is not intended, merely a detectable difference.

Preferably the markers of the present invention are, singly or in combination, more specific to the target tissue than are serum GH or IGF-1 levels, or than GH mRNA or IGF-1 mRNA levels in the target tissue.

If this specifications calls for alignment of DNA sequences, and one of the sequences is intended for the use as a hybridization probe, the sequences are to be aligned using a local alignment program with matches scored +5, mismatches scored −4, the first null of a gap scored −12, and each additional null of the same gap scored −2. Percentage identity is the number of identities expressed as a percentage of the length of the overlap, including internal gaps.

In Vitro Assays

The in vitro assays of the present invention may be applied to any suitable analyte-containing sample, and may be qualitative or quantitative in nature.

For the techniques to practice these assays, see, in general, Ausubel, et al., *Current Protocols in Molecular Biology*, and in particular chapters 2 ("Preparation and Analysis of DNA"), 3 ("Enzymatic Manipulation of DNA and RNA"), 4 ("Preparation and Analysis of RNA"), 5 ("Construction of Recombinant DNA libraries") 6 ("Screening of Recombinant DNA Libraries"), 7 ("DNA Sequencing"), 10 ("Analysis of Proteins"), 11 ("Immunology"), 14 ("In situ hybridization and immune histochemistry"), 15 ("The Polymerase Chain Reaction"), 19 ("Informatics for Molecular Biologists"), and 20 ("Analysis of Protein Interactions"). Also see, in general, Coligan, et al., *Current Protocols in Immunology*, and in particular, chapters 2 ("Induction of immune responses"), 8 ("Isolation and Analysis of Proteins"), 9 ("Peptides"), 10 ("Molecular Biology") and 17 ("Engineering Immune Molecules and Receptors"). Also see Coligan, et al., *Current Protocols in Protein Science*.

The Assay Target (Marker) (Analyte)

In one embodiment, the assay target is a messenger RNA transcribed from a gene which, in liver cells, has increased transcriptional activity if serum GH levels are increased. This messenger RNA may be a full length transcript of the gene, or merely a partial transcript. In the latter case, it must be sufficiently long so that it is possible to achieve specific binding, e.g., by nucleic acid hybridization. For the purpose of conducting the assay, the messenger RNA is extracted from liver cells by conventional means. Alternatively, the assay target may be a complementary DNA synthesized in vitro from the messenger RNA as previously described.

For convenience, the term "gene" or "target sequence" will be used to refer to the messenger RNA or complementary DNA corresponding to the induced gene, and to the coding gene proper.

In another embodiment, the assay target is a protein encoded by said gene and expressed at higher levels in response to elevated GH levels. If the protein is secreted, the assay may be performed on serum. If the protein is not secreted, then liver cells will be obtained from the subject and lysed to expose the cytoplasmic contents.

In either embodiment, one or more purification steps may be employed prior to the practice of the assay in order to enrich the sample for the assay target.

The proteins of particular interest are as follows:
alpha-fetoprotein
fetuin
3-β-hydroxysteroid
rab8-interacting protein
paraoxonase-3
interferon α/β receptor
proteasome z-subunit
corticosteroid binding globulin
growth hormone receptor
cytochrome P450IIIA
cytochrome P450
coagulation factor V
S-2 hydroxyacid oxidase The genes of particular interest are those encoding the above proteins. These genes were identified, as described in Example 1, on the basis of the identity or similarity of mouse cDNAs obtained by subtractive hybridization methods to known mouse genes or cDNAs (or, in the case of the S-2 hydroxyacid oxidase, to a known rat gene). The mouse sequencens were transferred onto a nylon membrane. After transfer of RNA onto the membrane, the membrane may then be used in a hybridization reaction with a suitable probe, which may be a synthetic probe directed against a gene already known to be a marker, or which may be a cDNA probe prepared directly from subtractive hybridization, wherein the fragment encoding the gene of interest, that is enriched in GH-overproducing subjects, will be labeled, preferably either radioactively with $^{32}$P or non-radioactively with DIG (Digoxigenin). A negative control, such as one composed of RNA sample from liver of normal subjects, may be resolved side by side with the patients' sample, Detection of this gene or protein could therefore indicate the presence of liver problem.

Certainly newly discovered DNAs are also of interest. These are identified below as clones 5 and 45. The proteins encoded by the ORFs embedded in these DNAs are also of interest.

Samples

The sample may be of any biological fluid or tissue which is reasonably expected to contain the messenger RNA transcribed from one of the above genes, or a protein expressed from one of the above genes. The sample may be of liver tissue or interstitial fluid, or of a systemic fluid into which liver proteins are secreted.

A non-invasive sample collection will involve the use of urine samples from human subjects. Blood samples will also be obtained in order to obtained plasma or serum from which secreted proteins can be evaluated. Liver aspirates can also be obtained to detect for the presence of genes and proteins of interest. The most invasive method would involve obtaining liver biopsies.

Analyte Binding Reagents (Molecules, ABM)

When the assay target is a nucleic acid, the preferred binding reagent is a complementary nucleic acid. However, the nucleic acid binding agent may also be a peptide or protein. A peptide phage library may be screened for peptides which bind the nucleic acid assay target. In a similar manner, a DNA binding protein may be randomly mutagenized in the region of its DNA recognition site, and the mutants screened for the ability to specifically bind the target. Or the hypervariable regions of antibodies may be mutagenized and the antibody mutants displayed on phage.

When the assay target is a protein, the preferred binding reagent is an antibody, or a specifically binding fragment of an antibody. The antibody may be monoclonal or polyclonal. It can be obtained by first immunizing a mammal with the protein target, and recovering either polyclonal antiserum, or immunocytes for later fusion to obtain hybridomas, or by constructing a n antibody phage library and screening the antibodies for binding to the target. The binding reagent may also be a binding molecule other than an antibody, such as a receptor fragment, an oligopeptide, or a nucleic acid. A suitable oligopeptide or nucleic acid may be identified by screening a suitable random library.

Binding and Reaction Assays

The assay may be a binding assay, in which one step involves the binding of a diagnostic reagent to the analyte, or a reaction assay, which involves the reaction of a reagent with the analyte. The reagents used in a binding assay may be classified as to the nature of their interaction with analyte: (1) analyte analogues, or (2) analyte binding molecules (ABM). They may be labeled or insolubilized.

In a reaction assay, the assay may look for a direct reaction between the analyte and a reagent which is reactive with the analyte, or if the analyte is an enzyme or enzyme inhibitor, for a reaction catalyzed or inhibited by the analyte. The reagent may be a reactant, a catalyst, or an inhibitor for the reaction.

An assay may involve a cascade of steps in which the product of one step acts as the target for the next step. These steps may be binding steps, reaction steps, or a combination thereof.

Signal Producing System (SPS)

In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

In a reaction assay, the signal is often a product of the reaction. In a binding assay, it is normally provided by a label borne by a labeled reagent.

Labels

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^3H$, $^{32}P$, $^{125}I$, $^{131}I$, $^{35}S$, $^{14}C$, and, preferably, $^{125}I$.

The label may also be a fluorophore. When the fluorescently labeled reagent is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}Eu$, or others of the lanthanide series, may be incorporated into a diagnostic reagent using such metal chelating groups as diethylenetriaminepentaacetic acid (DTPA) of ethylenediamine-tetraacetic acid (EDTA).

The label may also be a chemiluminescent compound. The presence of the chemiluminescently labeled reagent is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used for labeling. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase and alkaline phosphatase, are preferred. When an enzyme label is used, the signal producing system must also include a substrate for the enzyme. If the enzymatic reaction product is not itself detectable, the SPS will include one or more additional reactants so that a detectable product appears.

An enzyme analyte may act as its own label if an enzyme inhibitor is used as a diagnostic reagent.

Conjugation Methods

A label may be conjugated, directly or indirectly (e.g., through a labeled anti-ABM antibody), covalently (e.g., with SPDP) or noncovalently, to the ABM, to produce a diagnostic reagent. Similarly, the ABM may be conjugated to a solid phase support to form a solid phase ("capture") diagnostic reagent.

Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention.

The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Binding Assay Formats

Binding assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

In one embodiment, the ABM is insolubilized by coupling it to a macromolecular support, and analyte in the sample is allowed to compete with a known quantity of a labeled or specifically labelable analyte analogue. The "analyte analogue" is a molecule capable of competing with analyte for binding to the ABM, and the term is intended to include analyte itself. It may be labeled already, or it may be labeled subsequently by specifically binding the label to a moiety differentiating the analyte analogue from analyte. The solid and liquid phases are separated, and the labeled analyte analogue in one phase is quantified. The higher the level of analyte analogue in the solid phase, i.e., sticking to the ABM, the lower the level of analyte in the sample.

In a "sandwich assay", both an insolubilized ABM, and a labeled ABM are employed. The analyte is captured by the insolubilized ABM and is tagged by the labeled ABM, forming a ternary complex. The reagents may be added to the sample in either order, or simultaneously. The ABMs may be the same or different. The amount of labeled ABM in the ternary complex is directly proportional to the amount of analyte in the sample.

The two embodiments described above are both heterogeneous assays. However, homogeneous assays are conceivable. The key is that the label be affected by whether or not the complex is formed.

Detection of Genes of Interest

For the detection of genes in the sample, PCR can be performed using primers specific for the genes of interest. This would amplify the genes of interest. Primers may be designed to anneal to any site within the open reading frames of the genes of interest. Resolution of the fragments by electrophoresis on agarose gel may be used to determine the presence of the genes. PCR product may be quantitated by densitometry in order to estimate the concentration of the genes in the samples.

Detection of genes of interest may also be done by Northern blot analysis on liver biopsies. Tissue sample from patients may be obtained and the total RNA extracted using RNAStat 60. The total RNA sample may then be resolved on denaturing gel by electrophoresis and then transferred onto a nylon membrane. After transfer of RNA onto the membrane, the membrane may then be used in hybridization with a suitable probe, which may be a synthetic probe directed against a gene already known to be a marker, or which may be a cDNA probe prepared directly from subtractive hybridization, wherein the fragment encoding the gene of interest, that is enriched in GH-overproducing subjects, will be labeled, preferably either radioactively with $^{32}P$ or non-radiactively with DIG (Digoxigenin). A negative control, such as one composed of RNA sample from liver of normal subjects, may be resolved side by side with the patients' sample, to determine quantitatively whether there is a significant increase in the level of gene expression. Elevation of the messenger RNA transcript from this gene would imply that liver damage might have occurred.

The DNA sequences of the present invention may be used either as hybridization probes per se, or as primers for PCR.

In a hybridization assay, a nucleic acid reagent may be used either as a probe, or as a primer. For probe use, only one reagent is needed, and it may hybridize to all or just a part of the target nucleic acid. Optionally, more than one probe may be used to increase specificity. For the primer-based assay, two primers are needed. These hybridize the non-overlapping, separated segments of the target sequence. One primer hybridizes to the plus strand, and the other to the minus strand. By PCR techniques, the target nucleic acid region starting at one primer binding site and ending at the other primer binding site, along both strands, is amplified, including the intervening segment to which the primers do not hybridize. In a primer-based assay, the primer thus will not correspond to the entire target, but rather each primer will correspond to one end of the target sequence.

In probe-based assays, hybridizations may be carried out on filters or in solutions. Typical filters are nitrocellulose, nylon, and chemically-activated papers. The probe may be double stranded or single stranded, however, the double stranded nucleic acid will be denatured for binding.

To be successful, a hybridization assay, whether primer- or probe-based, must be sufficiently sensitive and specific to be diagnostically useful.

For probe-based assays, sensitivity is affected by the amount and specific activity of the probe, the amount of the target nucleic acid, the detectability of the label, the rate of hybridization, and the duration of the hybridization. The hybridization rate is maximized at a Ti (incubation temperature) of 20–25° C. below Tm for DNA:DNA hybrids and 10–15° C. below Tm for DNA:RNA hybrids. It is also maximized by an ionic strength of about 1.5M $Na^+$. The rate is directly proportional to duplex length and inversely proportional to the degree of mismatching.

For primer-based PCR assays, sensitivity is not usually a major issue because of the extreme amplification of the signal.

For probe-based assays, specificity is a function of the difference in stability between the desired hybrid and "background" hybrids. Hybrid stability is a function of duplex length, base composition, ionic strength, mismatching, and destabilizing agents (if any).

The Tm of a perfect hybrid may be estimated. for DNA:DNA hybrids, as $Tm=81.5°$ C.$+16.6(\log M)+0.41(\%GC)-0.61(\%$ form$)-500/L$ and for DNA:RNA hybrids, as $Tm=79.8°$ C.$+18.5(\log M)+0.58(\%GC)-11.8(\%GC)^2-0.56(\%$ form$)-820/L$ where M, molarity of monovalent cations, 0.01–0.4 M NaCl, %GC, percentage of G and C nucleotides in DNA, 30%–75%, % form, percentage formamide in hybridization solution, and L, length hybrid in base pairs.

Tm is reduced by 0.5–1.5° C. for each 1% mismatching.

Tm may also be estimated by the method of Tinoco et al., developed originally for the determination of the stability of a proposed secondary structure of an RNA. Tm may also be determined experimentally.

Filter hybridization is typically carried out at 68° C., and at high ionic strength (e.g., 5–6×SSC), which is nonstringent, and followed by one or more washes of increasing stringency, the last wash being of the ultimately desired stringency. The equations for Tm can be used to estimate the appropriate Ti for the final wash, or the Tm of the perfect duplex can be determined experimentally and Ti then adjusted accordingly.

While a mouse cDNA was used to probe a mouse liver cDNA library, and could be used to probe nonmurine liver cDNA libraries, it would be expected that there would be some sequence divergence between cognate mouse and nonmouse DNAs, possibly as much as 25–50%.

Hence, when the human DNA cognate to the original mouse cDNA is known, it is better to use that DNA, or a fragment thereof, to probe a human liver cDNA library. The practitioner may use the complete genomic DNA or cDNA sequence of the human gene as a probe, or, for the sake of greater specificity or synthetic convenience, a partial sequence.

It is also noted that while some of the mouse clones were identical to subsequences of a databank mouse DNA, others diverged slightly. This divergence (up to 5%) could be artifactual (sequencing error) or real (allelic variation).

Hybridization conditions should be chosen so as to permit allelic variations, but avoid hybridizing to other genes. In general, stringent conditions are considered to be a Tm of 5° C. below the Tm of a perfect duplex, and a 1% divergence corresponds to a 1–1.5° C. reduction in Tm. Hence, use of a Tm of 5–15° C. below the Tm of the double stranded form of the probe is recommended.

If the sequences of the major allelic variants are known, one may use a mixed probe, and optionally increase the stringency.

If there is no known human gene cognate to the mouse (or rat) gene homologous to the clone, then the mouse (or rat) gene, or other known nonhuman cognate gene, may be used as a probe. In this case, more moderate stringency hybridization conditions should be used. The nonhuman gene may be modified to obey a more human set of codon preferences.

Alternatively, the mouse (or rat) gene may be used once as a probe to isolate the human gene, and the human gene then used for diagnostic work. If a partial human cDNA is obtained, it may be used to isolate a larger human cDNA, and the process repeated as needed until the complete human cDNA is obtained.

For cross-species hybridization, the Ti should be reduced further, by about 0.5–1.5° C., e.g., 1° C., for each expected 1% divergence in sequence. The degree of divergence may be estimated from the known divergence of the most closely related pairs of known genes from the two species.

If the desired degree of mismatching results in a wash temperature less than 45° C., it is desirable to increase the salt concentration so a higher temperature can be used. Doubling the SSC concentration results in about a 17° C. increase in Tm, so washes at 45° C. in 0.1×SSC and 62° C. in 0.2×SSC are equivalent (1×SSC=0.15 M NaCl, 0.015M trisodium citrate, pH 7.0).

The person skilled in the art can readily determine suitable combinations of temperature and salt concentration to achieve this degree of stringency.

The hybridization conditions set forth in the Examples may be used as a starting point, and then made more or less stringent as the situation merits.

Examples of successful cross-species-hybridization experiments include Braun, et al., EMBO J., 8:701–9 (1989) (mouse v. human), Imamura, et al., Biochemistry, 30:5406–11 (1991) (human v. rat), Oro, et al, Nature, 336:493–6 (1988) (human v. *Drosophila*), Higuti, et al., Biochem. Biophys. Res. Comm., 178:1014–20 (1991) (rat v. human), Jeung, et al., FEBS Lett., 307:224–8 (1992) (rat, bovine v. human), Iwata, et al., Biochem. Biophys. Res. Comm., 182:348–54 (1992) (human v. mouse), Libert, et al., Biochem. Biophys. Res. Comm., 187:919–926 (1992) (dog v. human), Wang, et al., Mamm. Genome, 4:382–7 (1993) (human v. mouse), Jakubiczka, et al., Genomics, 17:732–5 (1993) (human v. bovine), Nahmias, et al., EMBO J., 10:3721–7 (1991) (human v. mouse), Potier, et al., J. DNA Sequencing and Mapping, 2:211–218 (1992) (rat v. human), Chan, et al., Somatic Cell Molec. Genet., 15:555–62 (1989) (human v. mouse), Hsieh, et al., Id., 579–590 (1989) (human, mouse v. bovine), Sumimoto, et al., Biochem. Biophys. Res. Comm., 165:902–6 (1989) (human v. mouse), Boutin, et al., Molec. Endocrinol., 3:1455–61 (1989) (rat v. human), He, et al., Biochem. Biophys. Res. Comm., 171:697–704 (1990) (human, rat v. dog, guinea pig, frog, mouse), Galizzi, et al., Int. Immunol., 2:669–675 (1990) (mouse v. human). See also Gould, et al., Proc. Nat. Acad. Sci. USA, 86:1934–8 (1989).

In general, for cross-species hybridization, Ti=25–35° C. below Tm. Wash temperatures and ionic strengths may be adjusted empirically until background is low enough.

For primer-based PCR assays, the specificity is most dependent on reagent purity.

The final considerations are the length and binding site of the probe. In general, for probe-based assays, the probe is preferably at least 15, more preferably at least 20, still more preferably at least 50, and most preferably at least 100 bases (or base pairs) long. Preferably, if the probe is not complementary to the entire gene, it targets a region low in allelic variation.

In general, for primer-based PCR assays, the primer is preferably at least 18–30 bases in length. Longer primers do no harm, shorter primers may sacrifice specificity. The distance between the primers may be as long as 10 kb, but is preferably less than 3 kb, and of course should taken into account the length of the target sequence (which is likely to be shorter for mRNA or cDNA than for genomic DNA). Preferably, primers have similar GC content, minimal secondary structure, and low complementarily to each other, particularly in the 3' region.

For theoretical analysis of probe design considerations, see Lathe, et al., J. Mol. Biol., 183:1–12 (1985).

Detection of Proteins of Interest

ELISA can be done on blood plasma or serum from patients using antibodies specific to the protein of interest. Samples will be incubated with primary antibodies on plates. This primary antibody is specific to the protein of interest.

Another method that can be conducted will involve the use of chemical or enzymatic reactions in which the protein of interest will act as a substrate (or, if the protein is an enzyme, as a catalyst) to cause a reaction that lead to the production of colored solution or emission of fluorescence. Spectrometric analysis can be done in order to determine the concentration of the proteins in the sample.

Western blot analysis can also be done on the plasma/serum, liver aspirate, liver biopsies or urine samples. This would involve resolving the proteins on an electrophoretic gel, such as an SDS PAGE gel, and transferring the resolved proteins onto a nitrocellulose or other suitable membrane. The proteins are incubated with a target binding molecule, such as an antibody.

This binding reagent may be labeled or not. If it is unlabeled, then one would also employ a secondary, labeled molecule which binds to the binding reagent. One approach involves avidinating one molecule and biotinylating the other. Another is for the secondary molecule to be a secondary antibody which binds the original binding reagent.

To improve detection of the specific protein, immunoprecipitation can be conducted. This typically will involve addition of a monoclonal antibody against the protein of interest to samples, then allowing the Ig-protein complex to precipitate after the addition of an affinity bead (ie antihuman Ig sepharose bead). The immunoprecipitates will undergo several washings prior to transfer onto a nitrocellulose membrane. The Western blot analysis can be perform using another antibody against the primary antibody used.

Interpretation of Assay Results

The assay may be used to predict the clinical state of the liver if the level of GH activity remains unchanged.

A scheme for the diagnostic interpretation of the level of the target in question is determined in a conventional manner by monitoring the level of GH, the level of the target, and the liver condition in a suitable number of patients, and correlating the level of the target at an earlier time point with the simultaneous or subsequent liver tissue state.

This correlation is then used to predict the future clinical state of the liver in new patients with high GH levels.

The diagnosis may be based on a single marker, or upon a combination of markers, which may include, besides the markers mentioned above, the level of GH or of IGF-1. A suitable combination may be identified by any suitable technique, such as multiple regression, factor analysis, or a neural network using the scaled levels of the markers as inputs and the current or subsequent liver state as an output.

In vivo Diagnostic Uses

Radio-labelled ABM which are not rapidly degraded in blood may be administered to the human or animal subject. Administration is typically by injection, e.g., intravenous or arterial or other means of administration in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as a guide.

Typically, the imaging is carried out on the whole body of the subject, or on that portion of the body or organ relevant to the condition or disease under study. The amount of radio-labelled ABM accumulated at a given point in time in relevant target organs can then be quantified.

A particularly suitable radio-detecting device is a scintillation camera, such as a gamma camera. A scintillation camera is a stationary device that can be used to image distribution of radio-labelled ABM. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radio-labelled ABM in the target organ at a discrete point in time. In most continuous (dynamic) studies, quantitative data is obtained by observing changes in distributions of radioactive decay in target organs over time. In other words, a time-activity analysis of the data will illustrate uptake through clearance of the radio-labelled binding protein by the target organs with time.

Various factors should be taken into consideration in selecting an appropriate radioisotope. The radioisotope must be selected with a view to obtaining good quality resolution upon imaging, should be safe for diagnostic use in humans and animals, and should preferably have a short physical half-life so as to decrease the amount of radiation received by the body. The radioisotope used should preferably be pharmacologically inert, and, in the quantities administered, should not have any substantial physiological effect.

The ABM may be radio-labelled with different isotopes of iodine, for example $^{123}I$, $^{125}I$, or $^{131}I$ (see for example, U.S.

Pat. No. 4,609,725). The extent of radio-labeling must, however be monitored, since it will affect the calculations made based on the imaging results (i.e. a diiodinated ABM will result in twice the radiation count of a similar monoiodinated ABM over the same time frame).

In applications to human subjects, it may be desirable to use radioisotopes other than $^{125}$I for labelling in order to decrease the total dosimetry exposure of the human body and to optimize the detectability of the labelled molecule (though this radioisotope can be used if circumstances require). Ready availability for clinical use is also a factor. Accordingly, for human applications, preferred radio-labels are for example, $^{99m}$Tc, $^{67}$Ga, $^{68}$Ga, $^{90}$Y, $^{111}$In, $^{113m}$In, $^{123}$I, $^{186}$Re, $^{188}$Re or $^{211}$At.

The radio-labelled ABM may be prepared by various methods. These include radio-halogenation by the chloramine-T method or the lactoperoxidase method and subsequent purification by HPLC (high pressure liquid chromatography), for example as described by J. Gutkowska et al in "Endocrinology and Metabolism Clinics of America: (1987) 16 (1):183. Other known method of radio-labelling can be used, such as IODOBEADS™.

There are a number of different methods of delivering the radio-labelled ABM to the end-user. It may be administered by any means that enables the active agent to reach the agent's site of action in the body of a mammal. Because proteins are subject to being digested when administered orally, parenteral administration, i.e., intravenous subcutaneous, intramuscular, would ordinarily be used to optimize absorption of an ABM, such as an antibody, which is a protein.

EXAMPLES

BLASTIN and BLASTP searches were performed with the default parameters match +1, mismatch −3, gap q=−5 r=−2, penalty q+rk for gap length k. For BLASTP, BLOSUM62 matrix with q=−1, r=−1, lambda ratio=0.85.

Preliminary results indicate that proteosome z-subunit, GH receptor, rab8 interacting protein, alpha-fetoprotein, fetuin are elevated in livers of GH TM when compared to NT, whereas, 3-beta-HSD is decreased. IFNR, CBG, clone 45 and clone 5 are expressed in GH TM and not in NT littermates.

Example 1

Introduction: GH-inducible Liver Genes for Diagnosis of GH Action on Liver Pathology Human growth hormone (hGH) upon binding to its receptor induces expression of a number of genes. These growth hormone (GH)-inducible genes can be identified in transgenic mice (TM) expressing bovine GH (bGH). These mice are twice as big as wild type (WT) mice and are also reported to show some form of liver pathology in their later stages of life. Our work aimed to create a library of liver GH inducible-genes in liver and to identify genes that are associated with the progression of liver disease that may eventually be use to diagnose pathologic liver in humans as observed on patients with acromegaly, liver cirrhosis, and viral infections causing hepatitis.

Production of Differentially Expressed cDNAs from GH TM by Subtractive Hybridization The method employed to determine the GH-inducible genes in bGH TM involves subtractive hybridization using Clontech's PCR-Select cDNA Subtraction kit. This method requires that mRNAs be isolated first and then converted into cDNAs. The mRNAs from liver of 60 days old bGH TM and WT mice were isolated by passing through oligo-dT columns (Invitrogen's Fastract 2.0) total RNAs prepared by RNAStat 60. Conversion of mRNAs to cDNAs involves the use of AMV reverse transcriptase (Clontech). The primer used for the first strand cDNA synthesis is 5' TTTTGTA-CAAGCTT 3' (SEQ ID NO:6) which binds to polyA tail of the mRNA. This primer introduces a unique restriction site Rsa 1 downstream of polyA tail. The second strand cDNA synthesis involves the use of an enzyme cocktail composed of RNase H, DNA polymerase and ligase enzymes.

Once the double-stranded cDNAs from bGH TM (tester) and WT (driver) were prepared, these two cDNA populations were subjected to RsaI digestion to produce shorter, blunt ended fragments. The tester was divided into two halves and each half was then ligated with different adaptors, adaptor 1 and adaptor 2R. These two adaptors have stretches of identical sequences (in bold characters) which serve as sites for binding of PCR primer 1 during the PCR amplification:

Adaptor 1:5'-CTAATACGACTCACTATAGGGCTCGAGCGGCC-GCCCGGGCAGGT-3'
(SEQ ID NO:1)
3'-GGCCCGTCCA-5'
(SEQ ID NO:2)
Adaptor 2R:5'-CTAATACGACTCACTATAGGGCAGCGTGGTCGC-GGCCGAGGT-3'
(SEQ ID NO:3)
3'-GCCGGCTCCA-5'
(SEQ ID NO:4)

Since only one end of the adaptors is phosphorylated, ligation of adaptors to tester cDNAs can occur only at the 5' ends of the cDNAs.

Isolation of differentially expressed genes from GH TM (tester) is achieved by performing two hybridization steps. The first hybridization step involved mixing each of the adapter ligated testers with excess of drivers. This resulted in annealing of identical ss cDNA fragments common to both the tester and driver. Differentially expressed sequences from GH TM that did not form hybrids with the driver sequences underwent a second hybridization step. This step involved mixing two reaction products from the first hybridization in the presence of more drive cDNA. This resulted in the formation of new hybrids between adaptor ligated ss cDNAs from GH TM. After fill in of the ends of these new hybrids using 50X Advantage cDNA polymerase mix (Clontech), primer sites for PCR primer 1(5'-CTAATACGACTCACTATAGGGC-3', bases 1–22 of SEQ ID NO:1) were generated.

Subtraction is achieved by preventing the tester-driver hybrid sequences from being amplified during PCR amplification while hybrids between testers with adaptor 1 and adaptor 2R can. Thus, those cDNA fragments that undergo PCR amplification correspond to differentially expressed GH TM.

Two steps of PCR amplification were conducted to enrich the pool of differentially expressed cDNA from GH TM. PCR primer 1 was used in the first PCR amplification at 94° C. for 25 sec followed by 27 cycles at three different temperatures of 94° C. for 10 sec, 66° C. for 30 sec, and 72° C. for 1.5 min. After the first PCR amplification step which resulted to exponential amplification of differentially expressed sequences from GH TM, nested PCR primer 1(5'-TCGAGCGGCCGCCCGGGCAGGT-3', bases 23–44 of SEQ ID NO:1) and nested PCR primer 2R(5'-AGCGTGGTCGCGGCCGAGGT-3', bases 23–42 of SEQ ID NO:3) were added to the first PCR amplified reaction mixture. Then the second PCR amplification step was conducted at 10–12 cycles of amplification at 94° C. for 10 sec, 68° C. for 30 sec and 72° C. for 1.5 min. to further enrich the differentially expressed sequence from GH TM. The integrity of the products from each manipulation was determined by gel electrophoresis of an aliquot of the reaction mixtures. The differentially expressed sequences obtained by subtractive hybridization were subcloned directly into PCR II cloning vector.

Subcloning and Sequencing of Differentially Expressed Subtraction Products

The pool of partial cDNA fragments was ligated into a pCR® 2.1 expression vector using the TA Cloning® Kit from Invitrogen®. The ligation mixture was subsequently transformed into Library Efficiency DH5α™ Competent Cells from Life Technologies. Ampicillin resistant colonies were propagated and plasmid DNA was extracted and purified using an alkaline lysis miniprep protocol (Birnhoim, H. C. 1983).

The purified plasmid DNAs containing different partial cDNA fragments were then sequenced using S labeled dNTPs and the T7 Sequenase™ version 2.0 DNA polymerase from Amersham Life Science Products. The sequencing primer, 5' TACTCAAGCTATGCATCAAG 3' (SEQ ID NO:5), hybridized to the pCR® 2.1 expression vector in the multiple cloning site ~60 bases 5' of the partial cDNA insert. The sequence data was analyzed and matched against known sequences using BLAST (Basic Local Alignment Search Tools), available through the National Centers for Biotechnology Information (NCBI) internet database. Our search results indicated that out of 56 sequences analyzed, 13 were identifiable as perfectly or almost perfectly identical to subsequences of known genes on the database. These GH-inducible genes in the liver of GH TM are mouse α-fetoprotein, fetuin, 3-β-Hydroxysteroid, rab8-interacting protein, paraoxonase-3, interferon α/β receptor (IFNR αβ), proteasome z-subunit, corticosteroid binding globulin (CBG), growth hormone receptor, cytochrome P450IIIA, cytochrome P450, and coagulation factor V, and rat S-2-hydroxyacid oxidase. It follows that the cognate human genes may be used as probes for observing GH-regulated expression of those genes in the liver, which genes are presumed to be regulated in a similar manner.

Northern Analysis of RNA Extracted from Wildtype and bGH Transgenic Mice

Total RNA was extracted and purified from the livers of both bGH trangenic and nontransgenic littermates. 60 day old mice were euthanized and dissected to obtain the tissues we needed. Tissues were then homogenized in 1 ml RNA STAT-60™ Total RNA/mRNA Isolation Reagent per 100 mg of tissue. The RNA was quantitated by spectrophotometry (O.D. 260/280) and electrophoresed on agarose-formaldehyde gels and transferred onto Boehringer-Mannheim nylon membranes. probes were generated using an EcoRI which cleaves out the partial cDNA insert from the plasmid DNAs. The fragments were purified using the Qiaex® II Agarose Gel Extraction Kit from Qiagen®. The purified fragments were then labeled using the Random Primed DNA Labeling Kit from Boehringer Mannheim. The membrane bound RNA was then hybridized with $\alpha^{32}P$ labeled DNA probes specific for the aforementioned partial cDNA sequences (see previous page). Preliminary results indicate that IFNR αβ and CBG mRNA are expressed in livers of GH TM and not in NT littermates.

Additional information on preparation of DIG-labeled probe for Northern blot analysis.

Non-radioactive DIG-labeled probe for Northern blot was constructed by amplification of the target sequence in the first PCR step followed incorporation of digoxigenin-11-UTP or DIG-UTP (Roche) on the antisense strand during the second PCR. In the construction of probe for used in the confirmation of differential gene expression in GH transgenic mice versus non-transgenic mice, fragments from subtractive hybridization that were subcloned into pCR2.1 cloning vector were PCR amplified using primers pCR 2.1A (5' ATTACGCCAAGCTTGGTACCG 3' (SEQ ID NO:11)) and PCR IIB (5' CCCTCTAGATGCATGCTC 3' (SEQ ID NO:12)). Incorporation of DIG-UTP is accomplished using primer pCR 2.1A or pCRIIB in the second PCR step. pBluescript plasmid with the 'full-length' cDNA 45 and cDNA 5 probes, respectively. T3 (5' AATTAACCCTCAC-TAAAGGG 3' (SEQ ID NO:13)) and mKS (5' CCTCGAG-GTCGACGGTATC 3' (SEQ ID NO:14)) primers were used for the first PCR amplification step and mKS primer for the second DIG-UTP incorporation step.

Example 2

A cDNA library was constructed from the liver of growth hormone (GH) trangenic mice. The cDNA that was used in the construction of the cDNA library was prepared from mRNAs, which was obtained from total RNA isolated from the liver of GH transgenic mice. The cDNA prepared was then used to produce the lambda zap (Stratagene) cDNA library. The titer of the amplified library was $10^9$ pfu/ml and the recombination efficiency determined to be 75%. Screening of the cDNA library for novel genes was done by probe hybridization of the nitrocellulose plaque lifts. The probe used in the screening was prepared by PCR amplification of gene fragment, which previously was identified by subtractive hybridization as differentially expressed in GH transgenic mice and not in wild type mice. After screening of approximately $2.5 \times 10^5$ plaques, five plaques that hybridized with the probe were purified and then the pBluescript plasmids, which contain the cDNA inserts, were excised out of the lambda zap vector utilizing helper phages following the manufacturer's protocol. The cDNA sequence of the insert was determined by "walking" through the sequence starting with T3 and KS primers complementary to sequences in the plasmid vector.

Clone 5

The sequencing of cDNA for one of the positive clones that hybridize with probe 5 is completed (Table 2A).

Using GeneRunner software program, the translational reading frames were determined. The DNA sequence (SEQ ID NO:7) of Clone 5 has several ORFs; the longest, corresponding to 1548 bases, encodes a protein of 515 amino acid residues (SEQ ID NO:8). All ORFs are set forth in Table 3B.

Using BLAST (Basic Local Alignment Search Tool) programs, which are designed to compare DNA and protein sequences available in the database, the DNA and the corresponding protein sequences were found to be novel.

Protein motif search utilizing PROSITE database indicate that the protein corresponding to the longest open reading frame in cDNA sequence of Clone 5 possess the following motifs: N-glycosylation, protein kinase C phosphorylation, casein kinase II phosphorylation, and amidation sites. The protein appears to have a signal peptide but no transmembrane region found. Thus, this protein encoded by the longest open reading from in Clone 5 could be cytoplasmic in location.

Clone 45

The sequencing of cDNA (SEQ ID NO:9) for one of the positive clones that hybridize with probe 45 is complete (Table 3A)

Using GeneRunner software program, the translational reading frames were determined. The DNA sequence of Clone 45 has several ORFs; the longest, corresponding to 1029 bases (SEQ ID NO:9) which encodes a protein of 342 amino acids (SEQ ID NO:10). All ORFs are set forth in Table 3B.

Using BLAST (Basic Local Alignment Search Tool) programs, which are designed to compare DNA and protein sequences available in the database, the DNA and the corresponding protein sequences were found to be novel.

Protein motif search utilizing PROSITE database indicates that the protein corresponding to the longest open reading frame in cDNA sequence of Clone 45 possess the following motifs: N-glycosylation, protein kinase C phosphorylation, casein kinase II phosphorylation, and amidation sites, as well as a Myc-type helix-loop-helix dimerization domain. The protein appears to have signal peptide at the N-terminal and transmembrane region close to the N-terminal. This could indicate that the protein encoded by longest open reading frame in Clone 45 is membrane bound and/or secreted.

Significance of the protein motifs found in novel cDNA sequences isolated from the livers of GH transgenic mice:

N-glycosylation: post-translational modification of proteins involving attachment of carbohydrate residues. This modification is seen in secreted and membrane proteins. Glycosylation is associated with lengthening biological life of a protein by decreasing its rate of clearance from the serum. For membrane bound proteins, carbohydrates are usually involve in interaction with other cells or molecules, such as immunoglobulins, cell surface receptors, and proteases.

Phosphorylation sites: site of attachment of phosphate group. Reversible phosphorylation-dephosphorylation of protein is associated with regulation of activity of the protein. Some proteins are activated when phosphorylated and inactivated when unphosphorylated, or vice versa.

N-myristoylation: (usually at the N-terminus) this protein modification involves addition of myristoyl group which is believed to cause some of the attached proteins to be loosely associated with membranes. Some myristoylated proteins are not associated with membranes to any significant extent. Some of myristoylated proteins such as protein kinases and phosphatases have important roles in modulating cellular metabolism.

Amidation: is usually seen on carboxy-terminus of peptide hormones. Enzymes involve in amidation reaction are usually found in secretory granules.

Myc-type, helix-loop-helix (HLH) dimerization domain: HLH dimerization domains are usually present in proteins that interact with DNA. Myc proteins are involve in growth regulation.

References

Creighton, T. E. 1993. Proteins: Structures and Molecular Properties, 2nd ed. W. H. Freeman and Co., NY, pp. 78–99.

Lewin, B. 1994. Gene V. Oxford University Press, NY, pp. 899–902.

Example 3

Assay for Using Mouse DNAs Presence of Genes from Liver of Human Patients

Total RNA Preparation Human Liver

Total RNA will be extracted from liver biopsy using 10 mL RNAStat60 per gram of liver tissue. To 15–20 ug of liver RNA isolates, 1×MOPS, formaldehyde, formamide and ethidium bromide will be added, heat denatured at 60° C. then loaded on a formamide containing denaturing 1% agarose gel. The RNA will then be resolved by electrophoresis at 50V for about 2–2½ h. After electrophoresis, the gel will be washed twice briefly with deionized water; then once with 0.05N NaOH, with 0.1M Tris at pH 7.5, and with 10×SSC at washing times of at least 30 min in each case.

The resolved RNA after electrophoresis will be transferred onto a nylon membrane by upward gradient adsorption using 10×SSC as transfer buffer. The RNA on the membrane will be UV crosslinked at 120 mJ, after which the RNA blots will be ready for hybridization.

B. Northern Blot Hybridization Involving Non-radioactive DIG-labeled Probe

Northern blot hybridization using digoxigenin (DIG)-labeled probe will be conducted to determine whether the genes of interest are present in liver RNA blots. The probes to be used for hybridization will be prepared from pCR2 clones, which contain as inserts the fragments isolated by subtractive hybridization of liver genes from GH mice versus WT mice. The sequence homology of the fragments to that of the human genes range from about 74% to 94%, which were obtained using the default parameters of Blast 2.0 sequence alignment version blastn 2.0.8.

1. Preparation of DIG-labeled Probe

The DIG-labelled probe preparation will require PCR amplification of the inserts in pCR2 clones using Taq polymerase as polymerization enzyme and pCR 2.1A and pCR 2B as primers. The conditions for PCR amplification will be 95° C. for 2 min.; 55 cycles at three temperature conditions of 95° C. for 15 sec., 58° C. for 20 sec., and 72° C. for 45 sec.; then 72° C. for 7 min. The amplified double-stranded cDNA fragment will undergo a second PCR amplification using a single primer, pCR 2.1A, in the presence of DIG labeled dNTPs to produce a single stranded DIG-labeled PCR product which will serve as the probe for RNA blot hybridization. The concentrations of the DIG labeled probe will be determined by comparing the signals produced by the probe to that of control DIG-labeled DNA upon exposure to radiographic film.

2. RNA Blot Hybridization

The concentration of DIG-labeled probe to be used for hybridization will be 50 ng/mL of DIG Easy Hyb solution (Boehringer-Mannheim). Prior to hybridization, the RNA blots will be prehybridized in DIG Easy Hyb solution at 42° C. for 30–60 min. Following prehybridization, the RNA blots will undergo hybridization using the probes prepared form the different pCR 2 clones. Hybridization will be done at 42° C. for at least 8 hours.

Posthybridization washings of the membrane will then be performed at room temperature for 5 min using a solution of 2×SSC and 0.1% SDS; and twice at 60° C. for 15 min. using a solution of 0.5×SSC and 0.1%SDS. The RNA blots will then be incubated with DIG antibody, which is conjugated to alkaline phosphatase. This antibody recognizes the DIG labeled hybrids in the RNA blot. CSPD (Boehringer-Mannheim), which is a chemiluminescent substrate for alkaline phosphatase, will be use to achieve detection of the RNA of interest in the blot. The presence of bands that is specific to the liver genes of interest could be diagnostic of liver damage.

Northern Blot Hybridization Involving $^{32}$P-labeled Probe

1. Preparation of $^{32}$P-labeled Probe

The $^{32}$P-labeled probe will be prepared by first isolating the cDNA fragments that were inserted into the pCR 2 vector by performing EcoRI restriction enzyme digestion. The fragments will be purified though a Qiaex$^R$ agarose gel extraction column (Qiagen). A 25 ng of the purified fragment will serve as a template for the production of single-stranded $^{32}$P-labeled probe using Random Primed DNA Labeling kit (Boehringer-Mannheim). The unincorporated dNTPs will be separated from the radiolabeled fragments using STE Select D G-25 column. The purified radiolabeld probe will then be quantified to determine the activity of the probe per ug of the DNA template. A good labeling of the template would have a specific activity range of $10^8$–$10^9$ cpm/ug of the template DNA.

2. RNA Blot Hybridization

Prior to hybridization, prehybridization of the RNA blots will be performed by incubating the membrane in prehybridization solution made up of 50% formamide, 1% SDS, 1M NaCl, and 10% Dextran sulfate for 1 hour at 42° C. Hybridization of the RNA blot with the $^{32}$P-labeled probes prepared will follow after prehybridization. This will be conducted at 42° C. for at least 8 hours. Washing of the blots will be conducted once with 2×SSC at room temp for 5 min. and then with 2×SSC, 0.1% SDS at 56° C. which could last for about 5 minutes to an hour depending on the intensity of the radiactive signal. Radiographic exposure of the blots will determine whether the genes of interest are present.

TABLE A

Human Genes (counterpart of Mouse Genes) regulated by Growth Hormone in Liver Tissue

| Genes | Nucleotide Accession No. | Protein Accession Number |
|---|---|---|
| Human alpha-fetoprotein | NM_001134 | NP_001125 |
|  | V01514 | CAA24758 |
| Human Fetuin (A2HS) |  | WOHU |
|  | M16961 | AAA51683 |
|  |  | P02765 |
|  |  | S04467 |
| Human 3-beta-hydroxysteroid Type 1 | M27137 | AAA36015 dehydrogenase |
| Human Rab8 Interacting protein-like 1 | NM_003618 | NP_003609 |
| Human Paraoxonase-3 | L48516 | AAC41996 |
| Human IFN alpha/Beta Receptor | A32391 | CAA02098 |
| Human GHR | AAA52555 | M28458 |
| Human Cytochrome P450 IIIA | NM_000777 | NM_000768 |
|  | X12387 | CAA30944 |
|  | M18907 | AAA35745 |
|  | J04449 | AAA35747 |
|  | NM_000765 | NP_000756 |
|  | M14096 | AAA35744 |
|  | NM_000776 | NM_000767 |
| Hunan proteasome z-subunit | D38048 | BAA07238 |
| Human Corticosteroid binding Globulin | NM_001756 | NP_001747 |
| Human Coagulation Factor V | M16967 | AAA52424 |
|  | NM_000130 | NP_000121 |
| Rat S-2-hydroxyacid oxidase | X67156 | CAA47629 |

TABLE B

Result of Blast Search

| Clone | Closest Match | Identities |
|---|---|---|
| 2 | Mouse alpha fetoprotein M16111 | 77/78 |
| 6 | Mouse fetuin |  |
|  | AJ002146 | 70/70 |
|  | S96534 | 78/78 |
| 7 | mouse 3-beta hydroxysteroid dehydogenase |  |
|  | M77015 | 78/78 |
| 13 | mouse rab8-interacting protein |  |
|  | U50595 | 66/66 |
| 14 | mouse paraoxonase-3 |  |
|  | L76193 | 64/64 |
| 21 | rat S2 hydroxyacid oxidase |  |
|  | X67156 | 58/65 |

TABLE B-continued

Result of Blast Search

| Clone | Closest Match | Identities |
|---|---|---|
| 26 | mouse interferon α/β receptor |  |
|  | M89641 | 78/79 |
|  | U06244 | 78/79 |
| 29 | mouse low MW GH receptor |  |
|  | M31680 | 59/61 |
|  | M33324 | 59/61 |
| 20 | mouse cytochrome P450 IIIA |  |
|  | X60452 | 62/64 |
| 36 | same | 69/78 |
| 39 | mouse cytochrome P450 III A |  |
|  | D26137 | 75/81 |
| 37 | mouse proteazome Z subunit |  |
|  | D83585 | 77/78 |
| 34 | corticosteroid-binding protein |  |
|  | X70533 | 46/46 |
| 35 | same |  |
|  | X70533 | 37/37 |
| 52 | same |  |
|  | X70533 | 121/123 |
| 49 | same |  |
|  | X70533 | 46/46 |
| 56 | mouse coagulation factor V | 104/106 |

TABLE 1 shows the sequence of each clone, and its BLASTN alignment to the known mouse (or rat) gene as found in a sequence databank, to which it appears to be most closely related. The known genes are as follows:

(A) mouse alpha-fetoprotein (WLAC #2)
(B) mouse fetuin (WLAC #6)
(C) mouse 3-β-hydroxysteroid (WLAC #7)
(D) mouse rab8 interacting protein (WLAC #13)
(E) mouse paraoxonase-3 (WLAC #14)
(F) rat S-2-hydroxyacid oxidase (WLAC #21)
(G) mouse interferon α/β receptor (WLAC #26)
(H) mouse growth hormone receptor (WLAC #29)
(I) mouse cytochrome P450IIIA (WLAC #20, #36)
(J) mouse cytochrome P450 (WLAC #39)
(K) mouse proteasome z-subunit (WLAC#37)
(L) mouse corticosteroid binding globulin ((WLAC #3, 34, 35, 52)
(M) mouse coagulation factor V (WLAC #56)

TABLE 2

(A) full-length single stranded nucleotide sequence of clone 5 and (B) ORFs 1–16 corresponding to clone 5.

TABLE 3

(A) full-length single stranded nucleotide sequence of clone 45 (B) ORFs 1–9 corresponding to clone 45.

TABLE 1

WLAC#2-fetoprotein
WLAC #2 SEQUENCE

TCCTAGGCTTCTTGCAGCCTCCACGAGAGTTGGGGTTGACACCTGAGGTGCTTTCTGGGTGTAGCGAACTAGAATGGCA

TTTTGGAATCCATATTCTCCACCGCCCTCC (SEQ ID NO:15)

Sequence 1 1c11seq_1 WLAC #2          Length 109 from:1 to = 109
Sequence 2 gi191764  Mouse alpha-fctoprotein mRNA, partial cds.
                                      Length 1254 from:1 to = 1254
NOTE: The statistics (bitscore and expect value) is calculated based on the size of nr
database
Score = 187 bits (97), Expect 2e-46
Identities = 99/100 (99%), Positives = 99/100 (99%)
Aligned query 1–100 to subject 1071–972.
WLAC #3, 34, 35, 52 Corticosteroid Binding Globulin
WLAC #3 SEQUENCE

CATTGGTGGGAGCCAGGTCTCGGTGAGAACTTGAATCCTCATCAGTGACAGCCTGGGTGGTC

CAGAGGCCACTGGTGCAGAGCCAGAAGAGACAGGTATACAGGGCGAGCGACATTGTTTTGG (SEQ ID NO:16)

Sequence 1 1c11seq_1 WLAC #3          Length 124 from:1 to = 124
Sequence 2 gi 298114 M. musculus mRNA for corticosteroid-binding globulin
                                      Length 1462 from:1 to = 1462
Score = 217 bits(113), Expect = 1e-55
Identities = 122/124 (98%), Positives = 122/224 (98%), Gaps = 1/124 (0%)
Aligned query 1–124 to subject 169–47.
WLAC #34 SEQUENCE

GGCAGCAGGCAGCACATTCCCTTCATCCAGTTGCAGCATGGCCTTGCTGGCGCTACCGCCCT

CCGCACCACGCCCTAAGCCGAATTCTGCCATACTATCCATCACACTGG (SEQ ID NO:17)

Sequence 1 1c11seq_1 WLAC #34         Length 110 from:1 to = 110
Sequence 2 gi 298114 M. musculus mRNA for corticosteriod-binding globulin
                                      Length 1462 from:1 to = 1462
Score = 89.1 bits (46), Expect = 8e-17
Identities = 46/46 (100%), Positives = 46/46 (100%)
Aligned query 1–46 to subject 116–1071.
WLAC #35 SEQUENCE

GCAACTGGATGAAGGGAATGTGCTGCCTGCTGCCACCAATGGAAATCCTGTACCGCCCTCCG

CACCACGCCCTAAGCCCGAATTCTGCAGTCTAT (SEQ ID NO:18)

Sequence 1 1c11seq_1 WLAC #35         Length 95 from: 1 to = 95
Sequence 2 gi 298114 M. musculus mRNA for corticosteriod-binding globulin
                                      Length 1462 from:1 to = 1462
Score = 85.3 bits (44), Expect = 9e-16
Identities = 50/53 (94%), Positives = 50/53 (94%)
Aligned query 1–53 to subject 1083–1135.
WLAC #52 SEQUENCE

GCCTGACTGGACCATCATGGGCACCTTCACTGTGCTTGTCTCATTCACATAGAAGTCCTCCT

CTCAGTATTTTCTGGGCTGAAGGGAAGTTTCCATATTCCTTTGAGGAAGAGTAGTTGAT (SEQ ID NO:19)

Sequence 1 1c11seq 1 WLAC #52         Length 121 from:1 to = 121
Sequence 2 gi 298114 M. musculus mRNA for corticosteriod-binding globulin
                                      Length 1462 from:1 to = 1462
Score = 206 bits (107), Expect = 4e-52
Identities = 121/123 (98%), Positives = 121/123 (98%), Gaps = 2/123 (1%)
Aligned query 1–121 to subject 747–625.
WLAC #6 SEQUENCE

GGGAGAGGCACATTTTGAGCCCGGGAAATCTCCACCACTTTGGGGTAGGTTCCATTATTCTG

TGTGTTGAAGCAGCCAGGGCAGTGTTGAC (SEQ ID NO:20)

Sequence 1 1c11seq 1  WLAC #6         Length 91 from:1 to = 91
Sequence 2 gi 2546994 Mus musculus fe_(Ahsg) gene, complete cds.
                                      Length 8946 from:1 to = 8496
Score = 117 bits (61), Expect = 1e-25
Identities = 78/84 (92%), Positives = 78/84 (92%), Gaps = 1/84 (1%)
Aligned query 9–91 to subject 4638–4555.

TABLE 1-continued

WLAC #7 3--Hydroxysteroid
WLAC #7 SEQUENCE

GGGTCAGTGACTGGCAAGGCTTTGGTGACTTGATTAAGGCACTAAATTGGCCTCTGTGTCAA

AAGAAGGCAACAGCACCTGTGTTGTGCTTTTATCCTTACTG (SEQ ID NO:21)

Sequence 1 1c11seq_1 WLAC #7           Length 103 from:1 to = 103
Sequence 2 gi 194006 Mouse 3-beta-hydroxysteroid dehydrogenase/delta-5-delta-4 isomerase mRNA sequence
                                       Length 1533 from:1 to = 1533
Score = 198 bits (103), Expect = 7e-50
Identities = 103/103 (100%), Positives = 103/103 (100%)
Aligned query 1–103 to subject 1325–1223.
WLAC #13 rab8 Interacting Protein
WLAC #13 SEQUENCE

GGAAAGATCCAACTGATAACCCCGGGGCACACAGCAACCTCTACATCCTCACGGGTCACCAGAGCA

GCTACTGAGCTATCTCCCCGATGACGCCAAGCCCTCGGCCTC (SEQ ID NO:22)

Sequence 1 1c11seq_1 WLAC #13          Length 108 from:1 to = 108
Sequence 2 gi1330327 Mus musculus Rab8-interacting protein mRNA, complete cds.
                                       Length 2466 from:1 to = 2466
Score = 127 bits (66), Expect = 2e-28
Identities = 66/66 (100%), Positives = 66/66 (100%)
Aligned query 9–74 to subject 2401–2466.
WLAC #14 Paraoxonase-3
WLAC #14 SEQUENCE

GGCATAGAACTGCTCTGGCCCAAGAACCACAATGTCATTCACACTCTTGAGAAGTTCATGTT

TTGAGATTTTCAGGTGGATGAGAGAGAGCGTTGTTGTTCTTCAAA (SEQ ID NO:23)

Sequence 1 1c11seq_1  WLAC #14         Length 107 from:1 to = 107
Sequence 2 gi 1333639 Mus musculus paraoxonase-3(pon3_mRNA, complete cds.
                                       Length 1121 from:1 to = 1121
Score = 162 bits (84), Expect = 7c-39
Identities = 101/107 (94%), Positives = 101/107 (94%), Gaps = 2/107 (1%)
Aligned query 1–107 to subject 537–433.
WLAC #20, #36 Cytochrome P450IIIA
WLAC #20 SEQUENCE

GGAGCATGAGTTTCCCTCAAGGAGTTCTGCTGAGTTCTTCAGAAAGGCAGTGTCTAAGAACA

TCAGATATG (SEQ ID NO:24)

Sequence 1 1c11seq_1 WLAC #20          Length 71 from:1 to = 71
Sequence 2 gi 50534  M. musculus mRNA for cytochrome P-450IIIA
                                       Length 1690 from:1 to = 1690
Score = 112 bits (58), Expect 4e-24
Identities = 62/64 (96%), Positives = 62/64 (96%)
Aligned query 1–64 to subject 1581–1644.
WLAC #36 SEQUENCE

AAAGGATCACAAAAGTCAACTATTAAAATCCCTTTGGCTTTCTCCACAAAGGGATCCTCTAA

ACTTGTTGAGGGAATCCCACATTCACTCCAAA (SEQ ID NO:25)

Sequence 1 1c11seq_1 WLAC #36          Length 93 from:1 to = 93
Sequence 2 gi 50534  M. musculus mRNA for cytochrome P-450IIIA
                                       Length 1690 from:1 to = 1690
Score = 94.9 bits (49), Expect 1e-18
Identities = 80/93 (86%), Positives = 80/93 (86%), Gaps = 1/93 (1%)
Aligned query 1–93 to subject 730–639.
WLAC #21 S-2-Hydroxy acid oxidase
WLAC #21 SEQUENCE

AACCCAAGTTCCTACAGCATCTTTGCAGCTGTTGATCTCACTCTTTCGTTCTATTGGAGAAA

CTACCGGCCCAGCAATGTCTTTG (SEQ ID NO:26)

Sequence 1 1c11seq_1 WLAC #21          Length 85 from:1 to = 85
Sequence 2 gi 311832 R. norvegicus mRNA for (s)-2-hydroxy acid oxidase
                                       Length 1648 from:1 to = 1648
Score = 79.5 bits (41), Expect = 4e-14
Identities = 75/87 (86%), Positives = 75/87 (86%), Gaps = 2/87 (2%)
Aligned query 1–85 to subject 125–211.

TABLE 1-continued

WLAC #26 Interferon α/β Receptor
WLAC #26 SEQUENCE

GGCCACACTGAGATCTTAAACAACGCCAGCTCCTCCAGTTAGTGTCCCTTTCTCCATGGTTC

AGTGACTTCTGGTCAGAAG (SEQ ID NO:27)

Sequence 1 1c11seq_1 WLAC #26        Length 82 from:1 to = 82
Sequence 2 gi 194111 Mus musculus interferon alpha/beta receptor (IFNAR) mRNA, complete cds.
                                      Length 3894 from:1 to = 3894
Score = 144 bits (75), Expect = 8e-34
Identities = 82/83 (98%), Positives = 82/83 (98%), Gaps = 1/83 (1%)
Aligned query 1–82 to subject 2222–2140.
WLAC #29 GHR
WLAC #29 SEQUENCE

TTGCTGGACCCGGGGGTCGTTTCACTGTTGACCGAAATAGTGCAACCTGATCCACCCATTGG

CCTAACTGGACTTTACTAAA (SEQ ID NO:28)

Sequence 1 1c11seq_1 WLAC #29        Length 82 from:1 to = 82
Sequence 2 gi 193508 Mouse high molecular weight growth hormone receptor/binding protein, complete cds.
                                      Length 2288 from:1 to = 2288
Score = 94.9 bits (49), Expect = 9e-19
Identities = 63/65 (96%), Positives = 63/65 (96%), Gaps = 2/65 (3%)
Aligned query 19–82 to subject 541–604.
WLAC #37 Proteasome z-subunit
WLAC #37 SEQUENCE

TGTCCTCACCGAGAAAGTTACCCCTCTGGAGATTGAGGTGCTAGAAGAGACTGTTCAGACAA

TGGATACTTCGTAATGGTG (SEQ ID NO:29)

Sequence 1 1c11seq_1 WLAC #37        Length 81 from:1 to = 81
Sequence 2 gi 1632754 Mouse mRNA proteasome Z subunit, complete cds.
                                      Length 969 from:1 to = 969
Score = 142bits (74), Expect 3e-33
Identities = 74/74 (100%), Positives = 74/74 (100%)
Aligned query 1–74 to subject 763–836.
WLAC #56 Coagulation Factor V
WLAC #56 SEQUENCE

TGTGGCTTCTGAAAAGGGTAGTTATGAAATAATAGCAGCAAATGGCGAAGACACAGATGTGG

ATAAGCTGACCAACAGTACCTCAAAATCAGAATATCACAGTACCGCCCTCCGCACCACGCCC

CTAAGCCCGAATTCTCGAGAT (SEQ ID NO:30)

TABLE 2A

Full-length nucleotide sequences of Clone 5
(5' → 3' direction of the + strand) (SEQ ID NO:7)

AAGACCCGCCATGTCTCTGCTGGCTACTGTACTGCTGCTCTGGGGG

TTCACTCTGGGCCCAGGAAATACTCTAATGCTCGATTCTGGCAGTG

AACCTAAACTATGGGCAGAGCCTCAGTCCCTGCTGGAACCCTGGG

CAAACCTGACCCTGGTGTGTGCAGTTGATTTGCCGACTAAGGTCTT

CGAGCTGATCCAGAACGGGTGGTTCCTGAGTCAAGTCCGACTTGA

GACACAGGTGCTGTCATACCGCTTTTCCCTGGGGGCCATTACAAGT

AACAACAGTGGCATCTACCGCTGCAGATGTGGCGTGGAACCCCCT

GTTGACATTCACCTGCCAGCACTGAACAAGTGGACCATGCTAAGC

AATGCTGTGGAGGTGACAGGGAAAGAGCCCTTGCCTCGGCCCTTG

GCTCATGCTGATCCAGTCGACTGGATCACACCTGGTGGCCTGCCTG

TATACGTGATGTGCCAGGTTGCAATGCGGGTGTGACCTACCTGCT

GAGGCAGGAAGGAGTGGATGGCGTCCAGAAACCTGATGTCCAGC

ACAAGGGAACAGCTGGCTTTTTAATCTACAAGCCTGGCAACTACA

GCTGCAGCTACCTAACCCATGCAGCAGGTGAACCCTCTGAGCCCA

GTGATATTGTGACCATCAAGATGTATGCCTCACAGGCTCCACCCAC

TCTGTGTTTGATGGGAAACTACCTAATGATCTACCCCCAGAAGACA

TATGAGACCCTTGCCTGCAAAGCTCCTCGGAATGCAGCTGAATTCC

AACTCAGGCAAGGAGGGAAGGTGCTGAAAATTCATGGGTTTAGCC

CCACCAGAGATGCTATCCTGTACTATGTGAACTTGAAGGAACTGG

ATAACCCAGGTCCTTTCACCTGCCGCTACCGGATGCACAAATACAT

GCACGTTTGGTCAGAGGACAGCAAGCCCGTAGAGTTAATGTGGAG

TGATGAGACTCTACAAGCTCCGGTACTTACTGCAGAGCCATCGAG

TABLE 2A-continued

Full-length nucleotide sequences of Clone 5 (5' → 3' direction of the + strand) (SEQ ID NO:7)

TAGGGACCTTGAGCCTGGTTCAACGGTGCAGCTTCGATGTACTGCA

CCCGTATCCGGCCTGCGCTTTGGCCTGCAACGCCAGGGCAAACCG

GAATTAGTTGTGGTGCAAATGCTGAATTCGTCTGGGACCGAAGCA

GTCTTTGAGCTGCACAATATCTCAACAATAGACTCTGGAAACTACA

GCTGTATCTACATGGAACAGGCACCGCCATTCTCAGGATCTTCTTC

CAGTGAGCCCGTGGAGCTGCGGGTGAATGGGCCACCACCCAAGCC

AAGGCTGGAAGCTCTGTGGAAAAGCACAGTACATCTGGGTCAGGA

AGCCATCTTTCGATGCCACGGCCATGTGCCTAGGGTCAGCATGGA

GCTGGTACGTGAGGGCTTTAAAACACCCTTCGCGGTGGCCTCCAC

AAGAAGCACCTCAGCTTACCTGAAGCTGCTCTTCGTCGGTCCCCAA

CATGCAGGCAACTACAGCTGCCGCTATACGGCCCTGCCGCCCTTC

ACATTTGAATCAGGGATCAGCGACCCTGTGGAGGTTATAGTAGAA

GGTTAGGCTCTCCTGAGCTGTGTTTGAGGTTTTGGGTTCTTAATAT

TTCCAGAGCTGTACACTGGCTAATTGCTTCACCAAGGTCAGTGTGG

AAAGGCCCTGTGGCAACTTGCTGAGTCAATGAAGCCATTTCTTTGT

CTAGGCCGCTAATGTGGCTGCAGACACAAAAAAAGTGTTCTTGGG

AAGGGTTCAAGACAGGTATAATACCCATTCTTCTCAATGTAAGAT

AACTTCATTTTCTCTGGACTTAATAAAGGTCAAGTAAAAACCCGTT

TAAAAAAAAAAAAAAAAAAAAAAAAAAAAAAAAAAAAAAAAAAA

AAAAAAAAAAAAAAAAAAAAAAAAAAAAAAAAAAAGCTTGA

CAAAA

TABLE 2B

Open Reading Frames found in Clone 5

MSLLATVLLLWGFTLGPGNTLMLDSGSEPKLWAEPQSLLEPWANLTL

VCAVDLPTKVFELIQNGWFLSQVRLETQVLSYRFSLGAITSNNSGIYR

CRCGVEPPVDIHLPALNKWTMLSNAVEVTGKEPLPRPLAHADPVDWI

TPGGLPVYVMCQVAMRGVTYLLRQEGVDGVQKPDVQHKGTAGFLI

YKPGNYSCSYLTHAAGEPSEPSDIVTIKMYASQAPPTLCLMGNYLMIY

PQKTYETLACKAPRNAAEFQLRQGGKVLKIHGFSPTRDAILYYVNLK

ELDNPGPFTCRYRMHKYMHVWSEDSKPVELMWSDETLQAPVLTAEP

SSRDLEPGSTVQLRCTAPVSGLRFGLQRQGKPELVVVQMLNSSGTEA

VFELHNISTIDSGNYSCIYMEQAPPFSGSSSSEPVELRVNGPPPKPRLEA

LWKSTVHLGQEAIFRCHGHVPRVSMELVREGFKTPFAVASTRSTSAY

LKLLFVGPQHAGNYSCRYTALPPFTFESGISDPVEVIVEG@

(SEQ ID NO:8)

MWLQTQKKCSWEGFKTGIIPILLNVR#(SEQ ID NO:31)

MYCTRIRPALWPATPGQTGISCGANAEFVWDRSSL&

TABLE 2B-continued

Open Reading Frames found in Clone 5

(SEQ ID NO: 32)

MQATTAAAIRPCRPSHLNQGSATLWRL@(SEQ ID NO:33)

MRLYKLRYLLQSHRVGTLSLVQRCSFDVLHPYPACALACNARANRN@

(SEQ ID N0:34)

MGHHPSQGWKLCGKAQYIWVRKPSFDATAMCLGSAWSWYVRALKHP

SRWPPQEAPQLT& (SEQ ID NO:35)

MKLSYIEKNGYYTCLEPFPRTLFLCLQPH@(SEQ ID NO:36)

MSSGGRSLGSFPSNTEWVEPVRHTS& (SEQ ID NO:37)

MGIIPVLNPSQEHFFCVCSHISGLDKEMASLTQQVATGPFHTDLGEAISQ

CTALEILRTQNLKHSSGEPNLLL#(SEQ ID NO:38)

MAVPVPCRYSCSFQSLLLRYCAAQRLLRSQTNSAFAPQLIPVCPGVAGQ

SAGRIRVQYIEAAPLNQAQGPYSMALQ#(SEQ ID NO:39)

MNFQHLPSLPELEFSCIPRSFAGKGLICLLGVDH@(SEQ ID NO:40)

MAVASKDGFLTQMYCAFPQSFQPWLGWWPIHPQLHGLTGRRS&

(SEQ ID NO:41)

KTRHVSAGYCTAALGVHSGPRKYSNARFWQ& (SEQ ID NO:42)

FCQAFFFFFFFFFFFFFFFFFFFFFFFFKRVFT& (SEQ ID NO:43)

FVKLFFFFFFFFFFFFFFFFFFFFFFFLNGFLLDLY#

(SEQ ID NO:44)

LSSFFFFFFFFFFFFFFFFFFFFFFFFF#(SEQ ID NO:45)

Note:
First 12 sequences are ORF starting from met to stop codon, the next four sequences were also identified as ORFs from the beginning of the sequence to the stop codon. QRF analysis conducted using GeneRunner version 3.05 software by Hastings Software, Inc.
@ = TAG, & = TGA, # = TAA

TABLE 3A

Full-length nucleotide sequence of Clone 45 (5' → 3' direction of the + strand)(SEQ ID NO:9)

GCTGAACTGAAGACCCGCCATGTCTCTGCTGGCTACTGTACTG

CTGCTCTGGGGTTTCACTCTGGACCCAGCAACGGATGCAGCCA

CCTGTACATTCAAGGATGCCATAAAAAACAATTCCTTGCCCAG

GCCCTGGATTTTGCCTTATCCTGTGCCTTGGATCATACCTGGC

CTGATCACGTCCGTGTTGTGCCTGGGGAGAGTGAAAGGGGCA

GCCTTCCTGCTGAGGCGGGAAGGAGATGATGACTTCCTAGAG

GTAGCTGAAAATACCACTGTTTTCGGGGATGAAACTCAGGCAG

GATACAGGGAACAAGCCATGTTTCGAGTCTATCAACCGGGCAA

CTACAGCTGCAGCTATCAAACTCACGGAGAATGTACCTCCTCT

ACGCCCAGTAGGATTGTGACCATCAAGAAGTTTGCCAAACCAC

CGCCACCCCTGCTGACCTCCTCAGAAAGTTCCACAGTGGAGCC

TABLE 3A-continued

Full-length nucleotide sequence of Clone 45 (5' → 3' direction of the + strand)(SEQ ID NO:9)

ACCCCACATGGCCCGTATGACCCTTCTCTGTTCCACTTTTCTG

AACGACGTTGAATTTCAGCTGAGGCAGGGAAAGCGTGAGATG

AAGGTCCTTATGTTCAGCACCAGCCCAGAGCAAGTCAACTTCT

ATCTGAAATTGTCAGACATGGGTGACCAGAGCCCCTTCACCTG

CCGCTACCGTCTAAGCAACATGACAGCTTGGTCGGAAGACAGT

GAGCCCGTAGAGCTAATGTGGAGCGACGAAAGACTACCAGCA

CCAGTGTTGACTGCAGAGCCATCGACGAATCAGAGCTTTGAGC

CGGGTTCGACGGTGCAGTTTCGATGTACCGCACCCAAGGCTG

GCCTACGCTTTGAGTCTGGCCTGCGCTTTGGCCTGCATACCGA

AGACTTGTATGAGCGCAGCCTGATCCAGATACTGAAGTCTTCT

GGTCATGAAACTGTATTCCAGCTGCAAAACCTCTCAGCCGCAG

ATTCTGCCAGCTACAGCTGCATCTATACTGAACTGAAACCACC

CTTCTCTGGATCTGCTCCCAGCAACCTTGTGCCTCTGATGGTG

GACGGATCCTACGAGTACTGAACTCCTATAGTAAACTGGAGCT

GCATTTTGTGGGTCCCGAACATACAGGAAACTATACCTGCCGT

TATACCTCCTGGCAGCCTGAGCCCGTCCACTCAGAGCCCAGCA

ACTCCGTGGAGCTCCTAGTGGAAGGTATGGCAGTGGTTGGGT

TTTGCCTCTTGATCTTTGTTGGACTATGCATTCAGTTAATTGTG

TGATCTAGCCTGGTATTCAAAGGCCCCGTGGCAGTTTGCTGAG

TCAAGTCACCTACTACTTTGTCTGGGAAACTGAAGTAGCTGCA

GACACAGGACCAAACATTGTTCTTGGAAAGAGCAGAAGACAG

ACGGGCAGAACTCCTATTCTTCCTGCTGCAAGATGTATTTCCC

TCAAACTCCCTCCACTTAATAAAGATCAAAAAAAAAAAAA

TABLE 3B

Open Reading Frames for Clone 45

MSLLATVLLLWGFTLDPATDAATCTFKDAIKNNSLPRPWILPYPV

PWIIPGLITSVLCLGRVKGAAFLLRREGDDDFLEVAENTTVFGDE

TQAGYREQAMFRVYQPGNYSCSYQTHGECTSSTPSRIVTIKKFAK

PPPPLLTSSESSTVEPPHMARMTLLCSTFLNDVEFQLRQGKREMK

VLMFSTSPEQVNFYLKLSDMGDQSPFTCRYRLSNMTAWSEDSEP

TABLE 3B-continued

Open Reading Frames for Clone 45

VELMWSDERLPAPVLTAEPSTNQSFEPGSTVQFRCTAPKAGLRFE

SGLRFGLHTEDLYERSLIQILKSSGHETVFQLQNLSAADSASYSCI

YTELKPPFSGSAPSNLVPLMVDGSYEY&

(SEQ ID NO:10)

MKLRQDTGNKPCFESINRATTAAAIKLTENVPPLRPVGL&

(SEQ ID NO:46)

MTRRLQYLDQAALIQVFGMQAKAQARLKA@(SEQ ID NO:47)

MWGGSTVELSEEVSRGGGGLANFLMVTILLGVEEVHSP&

(SEQ ID NO:48)

MALQSThVLVVFRRSTLALRAHCLPTKLSCCLDGSGR&

(SEQ ID NO:49)

MHSPTKIKRQNPTTAIPSTRSSTELLGSEWTGSGCQEV#

(SEQ ID NO:50)

AELKTRHVSAGYCTAALGFHSGPSNGCSHLYIQGCHKKQFLAQALDFALS

CALDHTWPDHVRVVPGESERGSLPAEAGRR& (SEQ ID NO:51)

FFFLIFIKWREFEGNTSCSRKNRSSARLSSALSKNNVWSCVCSYFSFPDK

VVGDLTQQTATGPLNTRLDHTIN& (SEQ ID NO:52)

MASLNVQVAASVAGSRVKPQSSSTVASRDMAGLQFS (SEQ ID NO:53)

Note:
First six sequences are ORFs starting from met to stop codon, the next two sequences were also identified as ORFs from the beginning of the sequence to the stop codon and the last ORF is the sequence starting from met to the end of the sequence. ORF analysis conducted using GeneRunner version 3.05 software by Hastings Software, Inc.

---

What is claimed is:

1. A method of screening a subject for increased risk of abnormal levels of growth hormone activity in the liver, which comprises
   (A) obtaining a sample of one or more liver cells from the individual,
   (B) assaying messenger RNA of said sample, or complementary DNA reverse transcribed from said messenger RNA, to determine the level of transcriptional activity of an alpha-fetoprotein gene in said cell and
   (C) correlating the level of activity with the risk of an abnormal level of GH activity in the liver of the subject.

2. A method of diagnosing abnormal levels of growth hormone (GH) activity in the liver, or of predicting a change in the condition of the liver in response to abnormal levels of GH activity therein, which comprises
   (A) obtaining a sample of one or more liver cells from a subject,
   (B) assaying messenger RNA of said sample, or complementary DNA reverse transcribed from said messenger RNA, to determine the level of transcriptional activity of an alpha-feto protein gene, and one or more of the following genes in said cell:
   fetuin gene
   3-β-hydroxysteroid gene
   rab8-interacting protein gene
   paraoxonase-3 gene
   interferon α/β receptor gene
   proteasome z-subunit gene
   corticosteroid binding globulin gene
   growth hormone receptor gene
   cytochrome P450IIIA gene
   cytochrome P450 gene
   coagulation factor V gene
   S-2 hydroxyacid oxidase gene
   human gene at least 50% identical to SEQ ID NO:7
   human gene corresponding to at least 50% identical to SEQ ID NO:9 and
   (C) correlating the level of activity with the level of GH activity in the liver of the subject or the expected change in the condition of the liver as a result of such GH activity of the subject.

3. A method of diagnosing abnormal levels of growth hormone (GH) activity in the liver, or of predicting a change in the condition of the liver in response to abnormal levels of GH activity therein, which comprises
   (A) obtaining a sample of one or more liver cells from a subject who has abnormal levels of serum IGF-1 and/or serum GH,
   (B) assaying messenger RNA of said sample, or complementary DNA reverse transcribed from said messenger RNA, to determine the level of transcriptional activity of an alpha-fetoprotein gene in said cell and
   (C) correlating the level of activity with the level of GH activity in the liver of the subject or the expected change in the condition of the liver as a result of such GH activity of the subject.

4. A method of diagnosing abnormal levels of growth hormone (GH) activity in the liver of a subject, or of predicting a change in the condition of the liver in response to abnormal levels of GH activity therein, which comprises
   (I) determining the level of serum IGF-1 and/or serum GH in a subject, and
   (II) determining the level of transcriptional activity of a gene in the liver of that subject, where that gene is one whose level of transcriptional activity is potentially associated with abnormal GH activity in the liver, by
   (A) obtaining a sample of one or more liver cells,
   (B) assaying messenger RNA of said sample, or complementary DNA reverse transcribed from said messenger RNA, to determine the level of transcriptional activity of an alpha-fetoprotein gene in said cell and
   (C) correlating the level of activity with the level of GH activity in the liver of the subject or the expected change in the condition of the liver as a result of such GH activity of the subject.

5. A method of screening an individual for increased risk of abnormal levels of growth hormone activity in the liver, which comprises
   (A) obtaining a sample from a subject, where said sample is expected to contain protein produced by the liver,
   (B) assaying the protein in said sample to determine the level of alpha-fetoprotein in said cell
   (C) correlating the level of expression with the risk of an abnormal level of GH activity in the liver of the subject.

6. A method of diagnosing abnormal levels of growth hormone (GH) activity in the liver, or of predicting a change in the condition of the liver in response to abnormal levels of GH activity therein, which comprises
   (A) obtaining a sample from a subject, where said sample is expected to contain protein produced by the liver,
   (B) assaying the protein in said sample to determine the level of expression of alpha feto protein, and one or more of the following proteins:
   fetuin
   3-β-hydroxysteroid
   rab8-interacting protein
   paraoxonase-3
   interferon α/β receptor
   proteasome z-subunit
   corticosteroid binding globulin
   growth hormone receptor
   cytochrome P450IIIA
   cytochrome P450
   coagulation factor V and
   S-2 hydroxyoxidase protein encoded by a gene corresponding to clone 5 in mice human protein at least 50% identical to SEQ ID NO:8, human protein at least 50% identical to SEQ ID NO:9, in said cell,
   (C) correlating the level of expression with the level of GH activity in the liver in the subject or the expected change in the condition of the liver as a result of such GH activity in the subject.

7. A method of diagnosing abnormal levels of growth hormone (GH) activity in the liver, or of predicting a change in the condition of the liver in response to abnormal levels of GH activity therein, which comprises
   (A) obtaining a sample from a subject, where said sample is expected to contain protein produced by the liver, and said subject has abnormal levels of serum IGF-1 and/or serum GH,
   (B) assaying the protein in said sample to determine the level of expression of alpha-fetoprotein
   (C) correlating the level of expression with the level of GH activity in the liver in the subject or the expected change in the condition of the liver as a result of such GH activity in the subject.

8. A method of diagnosing abnormal levels of growth hormone (GH) activity in the liver, or of predicting a change in the condition of the liver in response to abnormal levels of GH activity therein, which comprises (I) determining the level of serum IGF-1 and/or serum GH in the subject, and thereby ascertaining the level of growth hormone activity in the subject and (II) determining the level of liver expression of alpha feto protein, whose level of liver expression is potentially associated with abnormal GH activity in the liver, by (A) obtaining a sample from said subject, where said sample is expected to contain protein produced by the liver, (B) assaying the protein in said sample to determine the level of expression of alpha-fetoprotein (C) correlating the level of expression determined in (II) with the level of GH activity in the liver or the expected change in the condition of the liver as a result of such GH activity.

9. The method of claim 5 where the level of transcriptional activity of the fetuin gene or expression of fetuin is also determined.

10. The method of claim 5 where the level of transcriptional activity of the 3-β-hydroxysteroid gene or expression of 3-β-hydroxysteroid is also determined.

11. The method of claim 5 where the level of transcriptional activity of the rab8-interacting protein gene or expression of rab8-interacting protein is also determined.

12. The method of claim 5 where the level of transcriptional activity of the paraoxonase-3 gene or expression of paraoxonase-3 is also determined.

13. The method of claim 5 where the level of transcriptional activity of the interferon α/β receptor gene or expression of interferon α/β receptor is also determined.

14. The method of claim 5 where the level of transcriptional activity of the proteasome 2-subunit gene or expression of proteasome 2-subunit is also determined.

15. The method of claim 5 where the level of transcriptional activity of the corticosteroid binding globulin gene or expression of corticosteroid binding globulin is also determined.

16. The method of claim 5 where the level of transcriptional activity of the cytochrome P450IIA gene or expression of cytochrome P450IIA is also determined.

17. The method of claim 5 where the level of transcriptional activity of the cytochrome P450 in gene or expression of cytochrome P450 is also determined.

18. The method of claim 5 where the level of transcriptional activity of the coagulation factor v gene or expression of coagulation factor v is also determined.

19. The method of claim 5 where the level of transcriptional activity of the S-2 hydroxyacid oxidase gene or expression of hydroxyacid oxidase is also determined.

20. The method of claim 5 where the level of transcriptional activity of the gene corresponding to clone 5 in mice gene or expression of gene corresponding to clone 5 in mice is also determined.

21. The method of claim 5 where the level of transcriptional activity of the gene corresponding to clone 45 in mice gene or expression of gene corresponding to clone 45 in mice is also determined.

* * * * *

SEQUENCE LISTING

<160> NUMBER OF SEQ ID NOS: 53

<210> SEQ ID NO 1
<211> LENGTH: 44
<212> TYPE: DNA

```
<213> ORGANISM: Artificial Sequence
<220> FEATURE:
<223> OTHER INFORMATION: Description of Artificial Sequence: Synthetic
      adaptors for PCR

<400> SEQUENCE: 1
ctaatacgac tcactatagg gctcgagcgg ccgcccgggc aggt                           44

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      adaptors for PCR

<400> SEQUENCE: 2
acctgcccgg                                                                 10

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      adaptors for PCR

<400> SEQUENCE: 3
ctaatacgac tcactatagg gcagcgtggt cgcggccgag gt                             42

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      adaptors for PCR

<400> SEQUENCE: 4
acctcggccg                                                                 10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Sequencing
      primers

<400> SEQUENCE: 5
tactcaagct atgcatcaag                                                      20

<210> SEQ ID NO 6
<211> LENGTH: 14
<212> TYPE: DNA
<213> ORGANISM: Mouse

<400> SEQUENCE: 6
ttttgtacaa gctt                                                            14

<210> SEQ ID NO 7
<211> LENGTH: 1908
<212> TYPE: DNA
<213> ORGANISM: Mouse

<400> SEQUENCE: 7
```

-continued

| | |
|---|---|
| aagacccgcc atgtctctgc tggctactgt actgctgctc tggggttca ctctgggccc | 60 |
| aggaaatact ctaatgctcg attctggcag tgaacctaaa ctatgggcag agcctcagtc | 120 |
| cctgctggaa ccctgggcaa acctgaccct ggtgtgtgca gttgatttgc cgactaaggt | 180 |
| cttcgagctg atccagaacg ggtggttcct gagtcaagtc cgacttgaga cacaggtgct | 240 |
| gtcataccgc ttttcctgg gggccattac aagtaacaac agtggcatct accgctgcag | 300 |
| atgtggcgtg aaccccctg ttgacattca cctgccagca ctgaacaagt ggaccatgct | 360 |
| aagcaatgct gtggaggtga cagggaaaga gcccttgcct cggcccttgg ctcatgctga | 420 |
| tccagtcgac tggatcacac ctggtggcct gcctgtatac gtgatgtgcc aggttgcaat | 480 |
| gcggggtgtg acctacctgc tgaggcagga aggagtggat ggcgtccaga aacctgatgt | 540 |
| ccagcacaag ggaacagctg gcttttaat ctacaagcct ggcaactaca gctgcagcta | 600 |
| cctaacccat gcagcaggtg aaccctctga gcccagtgat attgtgacca tcaagatgta | 660 |
| tgcctcacag gctccaccca ctctgtgttt gatgggaaac tacctaatga tctacccca | 720 |
| gaagacatat gagacccttg cctgcaaagc tcctcggaat gcagctgaat tccaactcag | 780 |
| gcaaggaggg aaggtgctga aaattcatgg gtttagcccc accagagatg ctatcctgta | 840 |
| ctatgtgaac ttgaaggaac tggataaccc aggtcctttc acctgccgct accggatgca | 900 |
| caaatacatg cacgtttggt cagaggacag caagcccgta gagttaatgt ggagtgatga | 960 |
| gactctacaa gctccggtac ttactgcaga gccatcgagt agggaccttg agcctggttc | 1020 |
| aacggtgcag cttcgatgta ctgcacccgt atccggcctg cgctttggcc tgcaacgcca | 1080 |
| gggcaaaccg gaattagttg tggtgcaaat gctgaattcg tctgggaccg aagcagtctt | 1140 |
| tgagctgcac aatatctcaa caatagactc tggaaactac agctgtatct acatggaaca | 1200 |
| ggcaccgcca ttctcaggat cttcttccag tgagcccgtg gagctgcggg tgaatgggcc | 1260 |
| accacccaag ccaaggctgg aagctctgtg gaaaagcaca gtacatctgg gtcaggaagc | 1320 |
| catctttcga tgccacggcc atgtgcctag ggtcagcatg gagctggtac gtgagggctt | 1380 |
| taaaacaccc ttcgcggtgg cctccacaag aagcacctca gcttacctga gctgctctt | 1440 |
| cgtcggtccc caacatgcag gcaactacag ctgccgctat acggccctgc gcccttcac | 1500 |
| atttgaatca gggatcagcg accctgtgga ggttatagta gaaggttagg ctctcctgag | 1560 |
| ctgtgtttga ggttttgggt tcttaatatt tccagagctg tacactggct aattgcttca | 1620 |
| ccaaggtcag tgtggaaagg ccctgtggca acttgctgag tcaatgaagc catttctttg | 1680 |
| tctaggccgc taatgtggct gcagacacaa aaaagtgtt cttgggaagg gttcaagaca | 1740 |
| ggtataatac ccattcttct caatgtaaga taacttcatt ttctctggac ttaataaagg | 1800 |
| tcaagtaaaa acccgtttaa aaaaaaaaa aaaaaaaaa aaaaaaaaa aaaaaaaaa | 1860 |
| aaaaaaaaa aaaaaaaaa aaaaaaaaa aaaaaagct tgacaaaa | 1908 |

<210> SEQ ID NO 8
<211> LENGTH: 512
<212> TYPE: PRT
<213> ORGANISM: Mouse

<400> SEQUENCE: 8

Met Ser Leu Leu Ala Thr Val Leu Leu Leu Trp Gly Phe Thr Leu Gly
 1               5                  10                  15

Pro Gly Asn Thr Leu Met Leu Asp Ser Gly Ser Glu Pro Lys Leu Trp
             20                  25                  30

Ala Glu Pro Gln Ser Leu Leu Glu Pro Trp Ala Asn Leu Thr Leu Val

-continued

```
                35                  40                  45
Cys Ala Val Asp Leu Pro Thr Lys Val Phe Glu Leu Ile Gln Asn Gly
         50                  55                  60

Trp Phe Leu Ser Gln Val Arg Leu Glu Thr Gln Val Leu Ser Tyr Arg
 65                  70                  75                  80

Phe Ser Leu Gly Ala Ile Thr Ser Asn Asn Ser Gly Ile Tyr Arg Cys
                 85                  90                  95

Arg Cys Gly Val Glu Pro Val Asp Ile His Leu Pro Ala Leu Asn
                100                 105                 110

Lys Trp Thr Met Leu Ser Asn Ala Val Glu Val Thr Gly Lys Glu Pro
                115                 120                 125

Leu Pro Arg Pro Leu Ala His Ala Asp Pro Val Asp Trp Ile Thr Pro
        130                 135                 140

Gly Gly Leu Pro Val Tyr Val Met Cys Gln Val Ala Met Arg Gly Val
145                 150                 155                 160

Thr Tyr Leu Leu Arg Gln Glu Gly Val Asp Gly Val Gln Lys Pro Asp
                    165                 170                 175

Val Gln His Lys Gly Thr Ala Gly Phe Leu Ile Tyr Lys Pro Gly Asn
                180                 185                 190

Tyr Ser Cys Ser Tyr Leu Thr His Ala Ala Gly Glu Pro Ser Glu Pro
            195                 200                 205

Ser Asp Ile Val Thr Ile Lys Met Tyr Ala Ser Gln Ala Pro Pro Thr
        210                 215                 220

Leu Cys Leu Met Gly Asn Tyr Leu Met Ile Tyr Pro Gln Lys Thr Tyr
225                 230                 235                 240

Glu Thr Leu Ala Cys Lys Ala Pro Arg Asn Ala Ala Glu Phe Gln Leu
                    245                 250                 255

Arg Gln Gly Gly Lys Val Leu Lys Ile His Gly Phe Ser Pro Thr Arg
                260                 265                 270

Asp Ala Ile Leu Tyr Tyr Val Asn Leu Lys Glu Leu Asp Asn Pro Gly
            275                 280                 285

Pro Phe Thr Cys Arg Tyr Arg Met His Lys Tyr Met His Val Trp Ser
        290                 295                 300

Glu Asp Ser Lys Pro Val Glu Leu Met Trp Ser Asp Glu Thr Leu Gln
305                 310                 315                 320

Ala Pro Val Leu Thr Ala Glu Pro Ser Ser Arg Asp Leu Glu Pro Gly
                    325                 330                 335

Ser Thr Val Gln Leu Arg Cys Thr Ala Pro Val Ser Gly Leu Arg Phe
                340                 345                 350

Gly Leu Gln Arg Gln Gly Lys Pro Glu Leu Val Val Gln Met Leu
            355                 360                 365

Asn Ser Ser Gly Thr Glu Ala Val Phe Glu Leu His Asn Ile Ser Thr
        370                 375                 380

Ile Asp Ser Gly Asn Tyr Ser Cys Ile Tyr Met Glu Gln Ala Pro Pro
385                 390                 395                 400

Phe Ser Gly Ser Ser Ser Glu Pro Val Glu Leu Arg Val Asn Gly
                    405                 410                 415

Pro Pro Pro Lys Pro Arg Leu Glu Ala Leu Trp Lys Ser Thr Val His
                420                 425                 430

Leu Gly Gln Glu Ala Ile Phe Arg Cys His Gly His Val Pro Arg Val
            435                 440                 445

Ser Met Glu Leu Val Arg Glu Gly Phe Lys Thr Pro Phe Ala Val Ala
        450                 455                 460
```

```
Ser Thr Arg Ser Thr Ser Ala Tyr Leu Lys Leu Leu Phe Val Gly Pro
465                 470                 475                 480

Gln His Ala Gly Asn Tyr Ser Cys Arg Tyr Thr Ala Leu Pro Pro Phe
                485                 490                 495

Thr Phe Glu Ser Gly Ile Ser Asp Pro Val Glu Val Ile Val Glu Gly
            500                 505                 510
```

<210> SEQ ID NO 9
<211> LENGTH: 1453
<212> TYPE: DNA
<213> ORGANISM: Mouse

<400> SEQUENCE: 9

```
gctgaactga agacccgcca tgtctctgct ggctactgta ctgctgctct ggggtttcac      60
tctggaccca gcaacggatg cagccacctg tacattcaag gatgccataa aaacaattc     120
cttgcccagg ccctggattt tgccttatcc tgtgccttgg atcatacctg cctgatcac     180
gtccgtgttg tgcctgggga gagtgaaagg ggcagccttc ctgctgaggc gggaaggaga    240
tgatgacttc ctagaggtag ctgaaaatac cactgttttc ggggatgaaa ctcaggcagg    300
atacagggaa caagccatgt ttcgagtcta tcaaccgggc aactacagct gcagctatca    360
aactcacgga gaatgtacct cctctacgcc cagtaggatt gtgaccatca gaagtttgc     420
caaaccaccg ccacccctgc tgacctcctc agaaagttcc acagtggagc cacccacat    480
ggcccgtatg acccttctct gttccacttt tctgaacgac gttgaatttc agctgaggca    540
gggaaagcgt gagatgaagg tccttatgtt cagcaccagc ccagagcaag tcaacttcta    600
tctgaaattg tcagacatgg gtgaccagag ccccttcacc tgccgctacc gtctaagcaa    660
catgacagct tggtcggaag acagtgagcc cgtagagcta atgtggagcg acgaaagact    720
accagcacca gtgttgactg cagagccatc gacgaatcag agctttgagc cgggttcgac    780
ggtgcagttt cgatgtaccg cacccaaggc tggcctacgc tttgagtctg gcctgcgctt    840
tggcctgcat accgaagact gtatgagcg cagcctgatc cagatactga agtcttctgg    900
tcatgaaact gtattccagc tgcaaaacct ctcagccgca gattctgcca gctacagctg    960
catctatact gaactgaaac cacccttctc tggatctgct cccagcaacc ttgtgcctct   1020
gatggtggac ggatcctacg agtactgaac tcctatagta aactggagct gcattttgtg   1080
ggtcccgaac atacaggaaa ctataccctgc cgttataccct cctggcagcc tgagcccgtc   1140
cactcagagc ccagcaactc cgtggagctc ctagtggaag gtatgcagt ggttgggttt    1200
tgcctcttga tctttgttgg actatgcatt cagttaattg tgtgatctag cctggtattc   1260
aaaggccccg tggcagtttg ctgagtcaag tcacctacta ctttgtctgg gaaactgaag   1320
tagctgcaga cacaggacca acattgttc ttggaaagag cagaagacag acgggcagaa    1380
ctcctattct tcctgctgca agatgtattt ccctcaaact ccctccactt aataaagatc   1440
aaaaaaaaaa aaa                                                      1453
```

<210> SEQ ID NO 10
<211> LENGTH: 342
<212> TYPE: PRT
<213> ORGANISM: Mouse

<400> SEQUENCE: 10

```
Met Ser Leu Leu Ala Thr Val Leu Leu Leu Trp Gly Phe Thr Leu Asp
 1               5                  10                  15
```

```
Pro Ala Thr Asp Ala Ala Thr Cys Thr Phe Lys Asp Ala Ile Lys Asn
            20                  25                  30
Asn Ser Leu Pro Arg Pro Trp Ile Leu Pro Tyr Pro Val Pro Trp Ile
        35                  40                  45
Ile Pro Gly Leu Ile Thr Ser Val Leu Cys Leu Gly Arg Val Lys Gly
    50                  55                  60
Ala Ala Phe Leu Leu Arg Arg Glu Gly Asp Asp Phe Leu Glu Val
65                  70                  75                  80
Ala Glu Asn Thr Thr Val Phe Gly Asp Glu Thr Gln Ala Gly Tyr Arg
                85                  90                  95
Glu Gln Ala Met Phe Arg Val Tyr Gln Pro Gly Asn Tyr Ser Cys Ser
            100                 105                 110
Tyr Gln Thr His Gly Glu Cys Thr Ser Ser Thr Pro Ser Arg Ile Val
        115                 120                 125
Thr Ile Lys Lys Phe Ala Lys Pro Pro Pro Leu Leu Thr Ser Ser
    130                 135                 140
Glu Ser Ser Thr Val Glu Pro Pro His Met Ala Arg Met Thr Leu Leu
145                 150                 155                 160
Cys Ser Thr Phe Leu Asn Asp Val Glu Phe Gln Leu Arg Gln Gly Lys
                165                 170                 175
Arg Glu Met Lys Val Leu Met Phe Ser Thr Ser Pro Glu Gln Val Asn
            180                 185                 190
Phe Tyr Leu Lys Leu Ser Asp Met Gly Asp Gln Ser Pro Phe Thr Cys
        195                 200                 205
Arg Tyr Arg Leu Ser Asn Met Thr Ala Trp Ser Glu Asp Ser Glu Pro
    210                 215                 220
Val Glu Leu Met Trp Ser Asp Glu Arg Leu Pro Ala Pro Val Leu Thr
225                 230                 235                 240
Ala Glu Pro Ser Thr Asn Gln Ser Phe Glu Pro Gly Ser Thr Val Gln
                245                 250                 255
Phe Arg Cys Thr Ala Pro Lys Ala Gly Leu Arg Phe Glu Ser Gly Leu
            260                 265                 270
Arg Phe Gly Leu His Thr Glu Asp Leu Tyr Glu Arg Ser Leu Ile Gln
        275                 280                 285
Ile Leu Lys Ser Ser Gly His Glu Thr Val Phe Gln Leu Gln Asn Leu
    290                 295                 300
Ser Ala Ala Asp Ser Ala Ser Tyr Ser Cys Ile Tyr Thr Glu Leu Lys
305                 310                 315                 320
Pro Pro Phe Ser Gly Ser Ala Pro Ser Asn Leu Val Pro Leu Met Val
                325                 330                 335
Asp Gly Ser Tyr Glu Tyr
            340
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primers

<400> SEQUENCE: 11
attacgccaa gcttggtacc g                                              21

<210> SEQ ID NO 12
<211> LENGTH: 18

<212> TYPE: DNA
<213> ORGANISM: Artificial Sequence
<220> FEATURE:
<223> OTHER INFORMATION: Description of Artificial Sequence: Synthetic
      primers

<400> SEQUENCE: 12
ccctctagat gcatgctc                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primers

<400> SEQUENCE: 13
aattaaccct cactaaaggg                                                 20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primers

<400> SEQUENCE: 14
cctcgaggtc gacggtatc                                                  19

<210> SEQ ID NO 15
<211> LENGTH: 109
<212> TYPE: DNA
<213> ORGANISM: Mouse

<400> SEQUENCE: 15
tcctaggctt cttgcagcct ccacgagagt tggggttgac acctgaggtg ctttctgggt     60
gtagcgaact agaatggcat tttggaatcc atattctcca ccgccctcc               109

<210> SEQ ID NO 16
<211> LENGTH: 123
<212> TYPE: DNA
<213> ORGANISM: Mouse

<400> SEQUENCE: 16
cattggtggg agccaggtct cggtgagaac ttgaatcctc atcagtgaca gcctgggtgg     60
tccagaggcc actggtgcag agccagaaga gacaggtata cagggcgagc gacattgttt    120
tgg                                                                  123

<210> SEQ ID NO 17
<211> LENGTH: 110
<212> TYPE: DNA
<213> ORGANISM: Mouse

<400> SEQUENCE: 17
ggcagcaggc agcacattcc cttcatccag ttgcagcatg gccttgctgg cgctaccgcc     60
ctccgcacca cgccctaagc cgaattctgc catactatcc atcacactgg              110

<210> SEQ ID NO 18
<211> LENGTH: 95
<212> TYPE: DNA
<213> ORGANISM: Mouse

```
<400> SEQUENCE: 18
gcaactggat gaagggaatg tgctgcctgc tgccaccaat ggaaatcctg taccgccctc      60
cgcaccacgc cctaagcccg aattctgcag tctat                                 95

<210> SEQ ID NO 19
<211> LENGTH: 121
<212> TYPE: DNA
<213> ORGANISM: Mouse

<400> SEQUENCE: 19
gcctgactgg accatcatgg gcaccttcac tgtgcttgtc tcattcacat agaagtcctc      60
ctctcagtat tttctgggct gaagggaagt ttccatattc ctttgaggaa gagtagttga     120
t                                                                    121

<210> SEQ ID NO 20
<211> LENGTH: 91
<212> TYPE: DNA
<213> ORGANISM: Mouse

<400> SEQUENCE: 20
gggagaggca cattttgagc ccgggaaatc tccaccactt tggggtaggt tccattattc      60
tgtgtgttga agcagccagg gcagtgttga c                                     91

<210> SEQ ID NO 21
<211> LENGTH: 103
<212> TYPE: DNA
<213> ORGANISM: Mouse

<400> SEQUENCE: 21
gggtcagtga ctggcaaggc tttggtgact tgattaaggc actaaattgg cctctgtgtc      60
aaaagaaggc aacagcacct gtgttgtgct tttatcctta ctg                       103

<210> SEQ ID NO 22
<211> LENGTH: 108
<212> TYPE: DNA
<213> ORGANISM: Mouse

<400> SEQUENCE: 22
ggaaagatcc aactgataac cccggggcac acagcaacct ctacatcctc acgggtcacc      60
agagcagcta ctgagctatc tccccgatga cgccaagccc tcggcctc                 108

<210> SEQ ID NO 23
<211> LENGTH: 107
<212> TYPE: DNA
<213> ORGANISM: Mouse

<400> SEQUENCE: 23
ggcatagaac tgctctggcc caagaaccac aatgtcattc acactcttga gaagttcatg      60
ttttgagatt tcaggtgga tgagagagag cgttgttgtt cttcaaa                    107

<210> SEQ ID NO 24
<211> LENGTH: 71
<212> TYPE: DNA
<213> ORGANISM: Mouse

<400> SEQUENCE: 24
ggagcatgag tttccctcaa ggagttctgc tgagttcttc agaaaggcag tgtctaagaa      60
```

-continued

```
catcagatat g                                                   71

<210> SEQ ID NO 25
<211> LENGTH: 93
<212> TYPE: DNA
<213> ORGANISM: Mouse

<400> SEQUENCE: 25
aaaggatcac aaaagtcaac tattaaaatc cctttggctt tctccacaaa gggatcctct    60
aaacttgttg agggaatcca cattcactcc aaa                                93

<210> SEQ ID NO 26
<211> LENGTH: 85
<212> TYPE: DNA
<213> ORGANISM: Mouse

<400> SEQUENCE: 26
aacccaagtt cctacagcat ctttgcagct gttgatctca ctctttcgtt ctattggaga    60
aactaccggc ccagcaatgt ctttg                                         85

<210> SEQ ID NO 27
<211> LENGTH: 81
<212> TYPE: DNA
<213> ORGANISM: Mouse

<400> SEQUENCE: 27
ggccacactg agatcttaaa caacgccagc tcctccagtt agtgtccctt tctccatggt    60
tcagtgactt ctggtcagaa g                                             81

<210> SEQ ID NO 28
<211> LENGTH: 82
<212> TYPE: DNA
<213> ORGANISM: Mouse

<400> SEQUENCE: 28
ttgctggacc cgggggtcgt ttcactgttg accgaaatag tgcaacctga tccacccatt    60
ggcctaactg gactttacta aa                                            82

<210> SEQ ID NO 29
<211> LENGTH: 81
<212> TYPE: DNA
<213> ORGANISM: Mouse

<400> SEQUENCE: 29
tgtcctcacc gagaaagtta cccctctgga gattgaggtg ctagaagaga ctgttcagac    60
aatggatact tcgtaatggt g                                             81

<210> SEQ ID NO 30
<211> LENGTH: 145
<212> TYPE: DNA
<213> ORGANISM: Mouse

<400> SEQUENCE: 30
tgtggcttct gaaagggta gttatgaaat aatagcagca aatggcgaag acacagatgt    60
ggataagctg accaacagta cctcaaaatc agaatatcac agtaccgccc tccgcaccac   120
gcccctaagc ccgaattctc gagat                                        145

<210> SEQ ID NO 31
<211> LENGTH: 26
```

<212> TYPE: PRT
<213> ORGANISM: Mouse

<400> SEQUENCE: 31

Met Trp Leu Gln Thr Gln Lys Lys Cys Ser Trp Glu Gly Phe Lys Thr
1               5                   10                  15

Gly Ile Ile Pro Ile Leu Leu Asn Val Arg
            20                  25

<210> SEQ ID NO 32
<211> LENGTH: 35
<212> TYPE: PRT
<213> ORGANISM: Mouse

<400> SEQUENCE: 32

Met Tyr Cys Thr Arg Ile Arg Pro Ala Leu Trp Pro Ala Thr Pro Gly
1               5                   10                  15

Gln Thr Gly Ile Ser Cys Gly Ala Asn Ala Glu Phe Val Trp Asp Arg
            20                  25                  30

Ser Ser Leu
        35

<210> SEQ ID NO 33
<211> LENGTH: 27
<212> TYPE: PRT
<213> ORGANISM: Mouse

<400> SEQUENCE: 33

Met Gln Ala Thr Thr Ala Ala Ala Ile Arg Pro Cys Arg Pro Ser His
1               5                   10                  15

Leu Asn Gln Gly Ser Ala Thr Leu Trp Arg Leu
            20                  25

<210> SEQ ID NO 34
<211> LENGTH: 46
<212> TYPE: PRT
<213> ORGANISM: Mouse

<400> SEQUENCE: 34

Met Arg Leu Tyr Lys Leu Arg Tyr Leu Leu Gln Ser His Arg Val Gly
1               5                   10                  15

Thr Leu Ser Leu Val Gln Arg Cys Ser Phe Asp Val Leu His Pro Tyr
            20                  25                  30

Pro Ala Cys Ala Leu Ala Cys Asn Ala Arg Ala Asn Arg Asn
        35                  40                  45

<210> SEQ ID NO 35
<211> LENGTH: 58
<212> TYPE: PRT
<213> ORGANISM: Mouse

<400> SEQUENCE: 35

Met Gly His His Pro Ser Gln Gly Trp Lys Leu Cys Gly Lys Ala Gln
1               5                   10                  15

Tyr Ile Trp Val Arg Lys Pro Ser Phe Asp Ala Thr Ala Met Cys Leu
            20                  25                  30

Gly Ser Ala Trp Ser Trp Tyr Val Arg Ala Leu Lys His Pro Ser Arg
        35                  40                  45

Trp Pro Pro Gln Glu Ala Pro Gln Leu Thr
    50                  55

<210> SEQ ID NO 36
<211> LENGTH: 29
<212> TYPE: PRT
<213> ORGANISM: Mouse

<400> SEQUENCE: 36

Met Lys Leu Ser Tyr Ile Glu Lys Asn Gly Tyr Tyr Thr Cys Leu Glu
1               5                   10                  15

Pro Phe Pro Arg Thr Leu Phe Leu Cys Leu Gln Pro His
            20                  25

<210> SEQ ID NO 37
<211> LENGTH: 25
<212> TYPE: PRT
<213> ORGANISM: Mouse

<400> SEQUENCE: 37

Met Ser Ser Gly Gly Arg Ser Leu Gly Ser Phe Pro Ser Asn Thr Glu
1               5                   10                  15

Trp Val Glu Pro Val Arg His Thr Ser
            20                  25

<210> SEQ ID NO 38
<211> LENGTH: 73
<212> TYPE: PRT
<213> ORGANISM: Mouse

<400> SEQUENCE: 38

Met Gly Ile Ile Pro Val Leu Asn Pro Ser Gln Glu His Phe Phe Cys
1               5                   10                  15

Val Cys Ser His Ile Ser Gly Leu Asp Lys Glu Met Ala Ser Leu Thr
            20                  25                  30

Gln Gln Val Ala Thr Gly Pro Phe His Thr Asp Leu Gly Glu Ala Ile
        35                  40                  45

Ser Gln Cys Thr Ala Leu Glu Ile Leu Arg Thr Gln Asn Leu Lys His
    50                  55                  60

Ser Ser Gly Glu Pro Asn Leu Leu Leu
65                  70

<210> SEQ ID NO 39
<211> LENGTH: 76
<212> TYPE: PRT
<213> ORGANISM: Mouse

<400> SEQUENCE: 39

Met Ala Val Pro Val Pro Cys Arg Tyr Ser Cys Ser Phe Gln Ser Leu
1               5                   10                  15

Leu Leu Arg Tyr Cys Ala Ala Gln Arg Leu Leu Arg Ser Gln Thr Asn
            20                  25                  30

Ser Ala Phe Ala Pro Gln Leu Ile Pro Val Cys Pro Gly Val Ala Gly
        35                  40                  45

Gln Ser Ala Gly Arg Ile Arg Val Gln Tyr Ile Glu Ala Ala Pro Leu
    50                  55                  60

Asn Gln Ala Gln Gly Pro Tyr Ser Met Ala Leu Gln
65                  70                  75

<210> SEQ ID NO 40
<211> LENGTH: 34
<212> TYPE: PRT
<213> ORGANISM: Mouse

-continued

```
<400> SEQUENCE: 40

Met Asn Phe Gln His Leu Pro Ser Leu Pro Glu Leu Glu Phe Ser Cys
 1               5                  10                  15

Ile Pro Arg Ser Phe Ala Gly Lys Gly Leu Ile Cys Leu Leu Gly Val
            20                  25                  30

Asp His

<210> SEQ ID NO 41
<211> LENGTH: 42
<212> TYPE: PRT
<213> ORGANISM: Mouse

<400> SEQUENCE: 41

Met Ala Val Ala Ser Lys Asp Gly Phe Leu Thr Gln Met Tyr Cys Ala
 1               5                  10                  15

Phe Pro Gln Ser Phe Gln Pro Trp Leu Gly Trp Trp Pro Ile His Pro
            20                  25                  30

Gln Leu His Gly Leu Thr Gly Arg Arg Ser
        35                  40

<210> SEQ ID NO 42
<211> LENGTH: 30
<212> TYPE: PRT
<213> ORGANISM: Mouse

<400> SEQUENCE: 42

Lys Thr Arg His Val Ser Ala Gly Tyr Cys Thr Ala Ala Leu Gly Val
 1               5                  10                  15

His Ser Gly Pro Arg Lys Tyr Ser Asn Ala Arg Phe Trp Gln
            20                  25                  30

<210> SEQ ID NO 43
<211> LENGTH: 35
<212> TYPE: PRT
<213> ORGANISM: Mouse

<400> SEQUENCE: 43

Phe Cys Gln Ala Phe Phe Phe Phe Phe Phe Phe Phe Phe Phe Phe Phe
 1               5                  10                  15

Phe Phe Phe Phe Phe Phe Phe Phe Phe Phe Phe Phe Phe Lys Arg
            20                  25                  30

Val Phe Thr
        35

<210> SEQ ID NO 44
<211> LENGTH: 38
<212> TYPE: PRT
<213> ORGANISM: Mouse

<400> SEQUENCE: 44

Phe Val Lys Leu Phe Phe Phe Phe Phe Phe Phe Phe Phe Phe Phe Phe
 1               5                  10                  15

Phe Phe Phe Phe Phe Phe Phe Phe Phe Phe Phe Phe Leu Asn Gly
            20                  25                  30

Phe Leu Leu Asp Leu Tyr
        35

<210> SEQ ID NO 45
<211> LENGTH: 29
```

```
<212> TYPE: PRT
<213> ORGANISM: Mouse

<400> SEQUENCE: 45

Leu Ser Ser Phe Phe Phe Phe Phe Phe Phe Phe Phe Phe Phe Phe
 1               5                  10                  15

Phe Phe Phe Phe Phe Phe Phe Phe Phe Phe Phe Phe
                20                  25

<210> SEQ ID NO 46
<211> LENGTH: 39
<212> TYPE: PRT
<213> ORGANISM: Mouse

<400> SEQUENCE: 46

Met Lys Leu Arg Gln Asp Thr Gly Asn Lys Pro Cys Phe Glu Ser Ile
 1               5                  10                  15

Asn Arg Ala Thr Thr Ala Ala Ala Ile Lys Leu Thr Glu Asn Val Pro
                20                  25                  30

Pro Leu Arg Pro Val Gly Leu
            35

<210> SEQ ID NO 47
<211> LENGTH: 29
<212> TYPE: PRT
<213> ORGANISM: Mouse

<400> SEQUENCE: 47

Met Thr Arg Arg Leu Gln Tyr Leu Asp Gln Ala Ala Leu Ile Gln Val
 1               5                  10                  15

Phe Gly Met Gln Ala Lys Ala Gln Ala Arg Leu Lys Ala
                20                  25

<210> SEQ ID NO 48
<211> LENGTH: 38
<212> TYPE: PRT
<213> ORGANISM: Mouse

<400> SEQUENCE: 48

Met Trp Gly Gly Ser Thr Val Glu Leu Ser Glu Val Ser Arg Gly
 1               5                  10                  15

Gly Gly Gly Leu Ala Asn Phe Leu Met Val Thr Ile Leu Leu Gly Val
                20                  25                  30

Glu Glu Val His Ser Pro
            35

<210> SEQ ID NO 49
<211> LENGTH: 37
<212> TYPE: PRT
<213> ORGANISM: Mouse

<400> SEQUENCE: 49

Met Ala Leu Gln Ser Thr Leu Val Leu Val Val Phe Arg Arg Ser Thr
 1               5                  10                  15

Leu Ala Leu Arg Ala His Cys Leu Pro Thr Lys Leu Ser Cys Cys Leu
                20                  25                  30

Asp Gly Ser Gly Arg
            35

<210> SEQ ID NO 50
<211> LENGTH: 38
```

```
<212> TYPE: PRT
<213> ORGANISM: Mouse

<400> SEQUENCE: 50

Met His Ser Pro Thr Lys Ile Lys Arg Gln Asn Pro Thr Thr Ala Ile
 1               5                  10                  15

Pro Ser Thr Arg Ser Ser Thr Glu Leu Leu Gly Ser Glu Trp Thr Gly
                20                  25                  30

Ser Gly Cys Gln Glu Val
                35

<210> SEQ ID NO 51
<211> LENGTH: 80
<212> TYPE: PRT
<213> ORGANISM: Mouse

<400> SEQUENCE: 51

Ala Glu Leu Lys Thr Arg His Val Ser Ala Gly Tyr Cys Thr Ala Ala
 1               5                  10                  15

Leu Gly Phe His Ser Gly Pro Ser Asn Gly Cys Ser His Leu Tyr Ile
                20                  25                  30

Gln Gly Cys His Lys Lys Gln Phe Leu Ala Gln Ala Leu Asp Phe Ala
            35                  40                  45

Leu Ser Cys Ala Leu Asp His Thr Trp Pro Asp His Val Arg Val Val
        50                  55                  60

Pro Gly Glu Ser Glu Arg Gly Ser Leu Pro Ala Glu Ala Gly Arg Arg
65                  70                  75                  80

<210> SEQ ID NO 52
<211> LENGTH: 73
<212> TYPE: PRT
<213> ORGANISM: Mouse

<400> SEQUENCE: 52

Phe Phe Phe Leu Ile Phe Ile Lys Trp Arg Glu Phe Glu Gly Asn Thr
 1               5                  10                  15

Ser Cys Ser Arg Lys Asn Arg Ser Ser Ala Arg Leu Ser Ser Ala Leu
                20                  25                  30

Ser Lys Asn Asn Val Trp Ser Cys Val Cys Ser Tyr Phe Ser Phe Pro
            35                  40                  45

Asp Lys Val Val Gly Asp Leu Thr Gln Gln Thr Ala Thr Gly Pro Leu
        50                  55                  60

Asn Thr Arg Leu Asp His Thr Ile Asn
65                  70

<210> SEQ ID NO 53
<211> LENGTH: 36
<212> TYPE: PRT
<213> ORGANISM: Mouse

<400> SEQUENCE: 53

Met Ala Ser Leu Asn Val Gln Val Ala Ala Ser Val Ala Gly Ser Arg
 1               5                  10                  15

Val Lys Pro Gln Ser Ser Thr Val Ala Ser Arg Asp Met Ala Gly
                20                  25                  30

Leu Gln Phe Ser
            35
```